United States Patent
Ardenkjaer-Larsen et al.

(10) Patent No.: US 6,466,814 B1
(45) Date of Patent: *Oct. 15, 2002

(54) METHOD OF MAGNETIC RESONANCE INVESTIGATION

(75) Inventors: Jan Henrik Ardenkjaer-Larsen; Oskar Axelsson; Klaes Golman; Lars-Goran Wistrand; Georg Hansson, all of Malmo (SE); Ib Leunbach, Dragor (DK); Stefan Petersson, Malmo (SE)

(73) Assignee: Amersham Health AS, Oslo (NO)

(*) Notice: Subject to any disclaimer, the term of this patent is extended or adjusted under 35 U.S.C. 154(b) by 34 days.

This patent is subject to a terminal disclaimer.

(21) Appl. No.: 09/609,153

(22) Filed: Jun. 30, 2000

Related U.S. Application Data

(63) Continuation of application No. PCT/GB98/03904, filed on Dec. 23, 1998.
(60) Provisional application No. 60/076,924, filed on Mar. 5, 1998.

(30) Foreign Application Priority Data

Jan. 5, 1998 (GB) ............................................. 9800158
Jun. 25, 1998 (GB) ............................................. 9813795

(51) Int. Cl.$^7$ ................................................. A61B 5/05
(52) U.S. Cl. ..................... 600/420; 600/419; 424/9.3; 324/307; 324/309
(58) Field of Search ................................. 600/410, 420, 600/419; 324/307, 309; 424/9.3

(56) References Cited

U.S. PATENT DOCUMENTS 5,617,859 A    4/1997   Souza et al.
6,278,893 B1 * 8/2001   Ardenkjaer-Larson et al. ... 600/420

FOREIGN PATENT DOCUMENTS

WO    0 355 884 A     2/1990
WO    WO 97 37239 A   10/1997
WO    WO 98/01766 A   1/1998
WO    WO 98 30918 A   7/1998

OTHER PUBLICATIONS

Chapellier M. et al., "First observation of a dynamic polarization of monolayers of He/sup 3/ adsorbed on fluorocarbon microspheres", Proceedings of the $17^{th}$ International Conference on Low Temperature Physics, Lt–17, Karlsruhe, West Germany, Aug. 15–22, 1984, XP002098873.

Langer S.A. et al., "A proposed method for polarizing liquid /sup 3/He", Journal of Low Temperature Physics, Nov. 1984, XP002098874.

Pietrass T. et al., "Optically polarized /sup 129/Xe in NMR spectroscopy", Advanced Materials, Oct. 1995, VCH Verlagsgesellschaft, Germany, XP002098966.

Disclosed anonymously, "The Use of Dynamically Polarized Contrast Agents", 4/93, XP002070308.

* cited by examiner

Primary Examiner—Ruth S. Smith
(74) Attorney, Agent, or Firm—Bacon & Thomas

(57) ABSTRACT

The present invention provides a method of magnetic resonance investigation of a sample, preferably of a human or non-human animal body. The method comprises the step of ex vivo polarization of a high $T_1$ agent. The polarizing agent is optionally separated from the high $T_1$ agent before the high $T_1$ agent is administered to the sample.

34 Claims, 5 Drawing Sheets

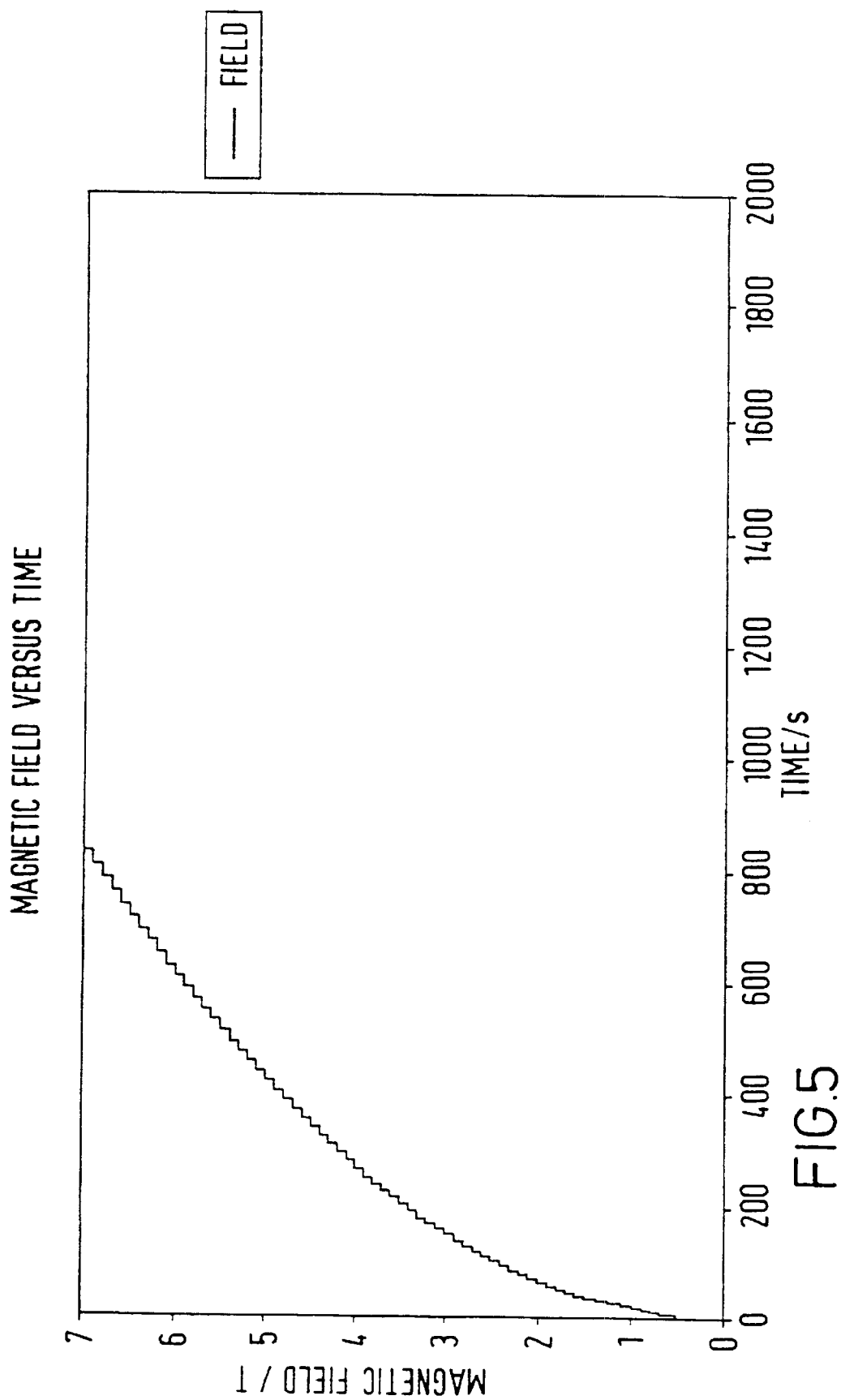

METHOD OF MAGNETIC RESONANCE INVESTIGATION

This application is a continuation of international application number PCT/GB98/03904, filed Dec. 23, 1998 (of which the entire disclosure of the pending, prior application is hereby incorporated by reference), which claims benefit of a continuation-in-part of U.S. provisional application No. 60/076,924, filed Mar. 5, 1998.

This invention relates to a method of magnetic resonance imaging (MRI).

Magnetic resonance imaging (MRI) is a diagnostic technique that has become particularly attractive to physicians as it is non-invasive and does not involve exposing the patient under study to-potentially harmful radiation such as X-rays.

In order to achieve effective contrast between MR images of the different tissue types in a subject, it has long been known to administer to the subject MR contrast agents (e.g. paramagnetic metal species) which effect relaxation times of the MR imaging nuclei in the zones in which they are administered or at which they aggregate. Contrast enhancement has also been achieved by utilising the "Overhauser effect" in which an esr transition in an administered paramagnetic species (hereinafter an OMRI contrast agent) is coupled to the nuclear spin system of the imaging nuclei. The Overhauser effect (also known as dynamic nuclear polarisation) can significantly increase the population difference between excited and ground nuclear spin states of selected nuclei and thereby amplify the MR signal intensity by a factor of a hundred or more allowing OMRI images to be generated rapidly and with relatively low primary magnetic fields. Most of the OMRI contrast agents disclosed to date are radicals which are used to effect polarisation of imaging nuclei in vivo.

EP-A-0355884 (to Hafslund Nycomed Innovation AB) discloses a method of and apparatus for performing electron spin resonance enhanced magnetic resonance imaging (ESREMRI) at ultra-low fields of up to 20 Gauss. Research Disclosure No. 348, April 1993, 242 (anon) discloses that electron paramagnetic resonance can result in the enhancement of an MR signal.

Techniques are now being developed which involve ex vivo polarisation of agents containing MR imaging nuclei, prior to administration and MR signal measurement. Such techniques may involve the use of polarising agents, for example conventional OMRI contrast agents or hyperpolarised gases to achieve ex vivo polarisation of administrable MR imaging nuclei. By polarising agent is meant any agent suitable for performing ex vivo polarisation of an MR imaging agent.

The ex vivo method has inter alia the advantage that it is possible to avoid administering the whole of, or substantially the whole of, the polarising agent to the sample under investigation, whilst still achieving the desired polarisation. Thus the method is less constrained by physiological factors such as the constraints imposed by the administrability, biodegradability and toxicity of OMRI contrast agents in in vivo techniques.

It has now been found that ex vivo methods of magnetic resonance imaging may be improved by using polarised MR imaging agents comprising nuclei capable of emitting magnetic resonance signals in a uniform magnetic field (eg MR imaging nuclei such as $^{13}C$ or $^{15}N$ nuclei) and capable of exhibiting a long $T_1$ relaxation time, preferably additionally a long $T_2$ relaxation time. Such agents will be referred to hereinafter as "high $T_1$ agents". Typically the molecules of a high $T_1$ agent will contain MR imaging nuclei in an amount greater than the natural abundance of said nuclei in said molecules (i.e. the agent will be enriched with said nuclei).

Thus viewed from one aspect the present invention provides a method of magnetic resonance investigation of a sample, preferably of a human or non-human animal body (eg. a mammalian, reptilian or avian body), said method comprising:

(i) producing a hyperpolarised solution of a high $T_1$ agent by dissolving in a physiologically tolerable solvent a hyperpolarised solid sample of said high $T_1$ agent;

(ii) where the hyperpolarisation of the solid sample of said high $T_1$ agent in step (i) is effected by means of a polarising agent, optionally separating the whole, substantially the whole, or a portion of said polarising agent from said high $T_1$ agent;

(iii) administering said hyperpolarised solution to said sample;

(iv) exposing said sample to radiation of a frequency selected to excite nuclear spin transitions in selected nuclei eg the MR imaging nuclei of the high $T_1$ agent;

(v) detecting magnetic resonance signals from said sample; and (vi) optionally, generating an image, dynamic flow data, diffusion data, perfusion data, physiological data (eg. pH, $PO_2$, $pCO_2$, temperature or ionic concentrations) or metabolic data from said detected signals, wherein said high $T_1$ agent in said hyperpolarised solution has a $T_1$ value (at a field strength in the range 0.01–5 T and a temperature in the range 20–40° C.) of at least 5 seconds and furthermore wherein said high $T_1$ agent is $^{13}C$ enriched at one or more carbonyl or quaternary carbon positions.

Thus the invention involves the sequential steps of producing a hyperpolarised solution from a hyperpolarised solid sample of a high $T_1$ agent comprising nuclei capable of exhibiting a long $T_1$ relaxation time, administration of the hyperpolarised solution of the high $T_1$ agent (preferably in the absence of a portion of, more preferably substantially the whole of, any polarising agent), and conventional in vivo MR signal generation and measurement. The MR signals obtained in this way may be conveniently converted by conventional manipulations into 2-, 3- or 4-dimensional data including flow, diffusion, physiological or metabolic data.

By "hyperpolarised" we mean polarised to a level over that found at room temperature and 1 T, preferably polarised to a polarisation degree in excess of 0.1%, more preferably 1%, even more preferably 10%.

Polarization is given by the equation $$P = \left| \frac{N\alpha - N\beta}{N\alpha + N\beta} \right|$$

which at equilibrium is equal to $$\frac{1 - \exp(-\gamma \hbar B_o / kT)}{1 + \exp(-\gamma \hbar B_o / kT)}$$

where $N\alpha$ is the number of spins in nuclear spin state $\alpha$ (e.g. $+\frac{1}{2}$);

$N\beta$ is the number of spins in nuclear spin state $\beta$ (e.g. $-\frac{1}{2}$);

$\gamma$ is the magnetogyric ratio for the isotopic nucleus in question, e.g. $^{13}C$;

$\hbar$ is Planck's constant divided by 2n;

$B_G$ is the magnetic field;

k is Boltzmann's constant; and
T is temperature in kelvin.

Thus P has a maximum value of 1 (100% polarization) and a minimum value of 0 (0% polarization).

By "physiologically tolerable solvent" we mean any solvent, solvent mixture or solution that is tolerated by the human or non-human animal body, e.g. water, aqueous solutions such as saline, perfluorocarbons, etc.

One embodiment of the invention provides a method as described above wherein the hyperpolarised solid sample of said high $T_1$ agent retains its polarisation when transported in a magnetic field and at low temperature; in this way the agent can be hyperpolarised at a site remote from its end use and transported to its place of use in a magnetic field and at a low temperature and there dissolved and administered.

In the embodiment referred to above, the magnetic field is preferably greater than 10 mT, more preferably greater than 0.1 T, even more preferably greater than 0.5 T, yet more preferably greater than 1 T. By "low temperature" we preferably mean lower than 80 K, more preferably lower than 4.2 K, most preferably lower than 1 K.

A further embodiment of the invention provides a method as described above wherein the hyperpolarised solution thus formed retains its polarisation when transported in a magnetic field. In this latest embodiment, the magnetic field is preferably greater than 10 mT, more preferably greater than 0.1 T, even more preferably greater than 0.5 T, yet more preferably greater than 1 T.

A yet further embodiment of the invention provides a method as described above wherein a magnetic field is present during the dissolution stage. In this latest embodiment, the magnetic field is preferably greater than 10 mT, more preferably greater than 0.1 T, even more preferably greater than 0.5 T, yet more preferably greater than 1 T.

Suitable high $T_1$ agents may contain nuclei such as protons. However other non-zero nuclear spin nuclei may be useful (eg $^{19}F$, $^3Li$, $^{13}C$, $^{15}N$, $^{29}Si$ or $^{31}P$, as well as $^1H$), preferably $^1H$, $^{13}C$, $^{15}N$, $^{19}F$, $^{29}Si$ and $^{31}P$ nuclei, with $^{13}C$ and $^{15}N$ nuclei being particularly preferred. In this event the MR signals from which the image is generated will be substantially only from the high $T_1$ agent itself. Nonetheless, where the polarised high $T_1$ agent is present in high concentration in administrable media, there may be significant enough transfer of magnetisation to the protons to be able to perform $^1$H-MRI on the protons of the media. Similarly, the polarised high $T_1$ agent may have a significant enough effect on in vivo protons for conventional $^1$H-MRI to be carried out on those protons.

Where the MR imaging nuclei is other than a proton (eg $^{13}C$ or $^{15}N$), there will be essentially no interference from background signals (the natural abundance of $^{13}C$ and $^{15}N$ being negligible) and image contrast will be advantageously high. This is especially true where the high $T_1$ agent itself is enriched above natural abundance. Thus the method according to the invention has the benefit of being able to provide significant spatial weighting to a generated image. In effect, the administration of a polarised high $T_1$ agent to a selected region of a sample (eg by injection) means that the contrast effect may be localised to that region. The precise effect of course depends on the extent of biodistribution over the period in which the high $T_1$ agent remains significantly polarised. In general, specific body volumes (i.e. regions of interest such as the vascular system or specific organs such as the brain, kidney, heart or liver) into which the agent is administered may be defined with improved signal to noise (particularly improved contrast to noise) properties of the resulting images in these volumes.

In one embodiment, a "native image" of the sample (e.g. body) (ie. one obtained prior to administration of the high $T_1$ agent or one obtained for the administered high $T_1$ agent without prior polarisation as in a conventional MR experiment) may be generated to provide structural (eg. anatomical) information upon which the image obtained in the method according to the invention may be superimposed. A "native image" is generally not available where $^{13}C$ or $^{15}N$ is the imaging nucleus because of the low abundance of $^{13}C$ and $^{15}N$ in the body. In this case, a proton MR image may be taken to provide the anatomical information upon which the $^{13}C$ or $^{15}N$ image may be superimposed.

The high $T_1$ agent should of course be physiologically tolerable or be capable of being provided in a physiologically tolerable, administrable form. Preferred high $T_1$ agents are soluble in aqueous media (eg. water) and are of course non-toxic where the intended end use is in vivo.

Conveniently, the high $T_1$ agent once polarised will remain so for a period sufficiently long to allow the imaging procedure to be carried out in a comfortable time span. Generally sufficient polarisation will be retained by the high $T_1$ agent in its administrable form (eg. in injection solution) if it has a $T_1$ value (at a field strength of 0.01–5 T and a temperature in the range 20–40° C.) of at least 5 s, more preferably at least 10 s, especially preferably 30 s or longer, more especially preferably 70 s or more, yet more especially preferably 100 s or more (for example at 37° C. in water at 1 T and a concentration of at least 1 mM). The high $T_1$ agent may be advantageously an agent with a long $T_2$ relaxation time.

The long $T_1$ relaxation time of certain $^{13}C$ nuclei is particularly advantageous and certain high $T_1$ agents containing $^{13}C$ nuclei are therefore preferred for use in the present method. The γ-factor of carbon is about ¼ of the γ-factor for hydrogen resulting in a Larmor frequency of about 10 MHz at 1 T. The rf-absorption and reflections in a patient is consequently and advantageously less than in water (proton) imaging. The signal-to-noise ratio is found to be independent of the MRI field strength when the corresponding frequency is higher than a few MHz. Preferably the polarised high $T_1$ agent has an effective $^{13}C$ nuclear polarisation corresponding to the one obtained at thermal equilibrium at 300 K in a field of 0.1 T or more, more preferably 25 T or more, particularly preferably 100 T or more, especially preferably 5000 T or more (for example 50 kT)

When the electron cloud of a given molecule interacts with atoms in surrounding tissue, the shielding of the atom responsible for the the MR signal is changed giving rise to a shift in the MR frequency ("the chemical shift effect"). When the molecule is metabolised, the chemical shift will be changed and high $T_1$ agents in different chemical surroundings may be visualised separately using pulses sensitive to chemical shift. When the frequency difference between high $T_1$ molecules in different surroundings is 10 Hz or higher, preferably 20 Hz or higher, most preferably 150 Hz or higher (corresponding to 3.5 ppm or higher at 1 T), the two components may be excited separately and visualised in two images. Standard chemical shift selective excitation pulses may then be utilised. When the frequency separation is less, the two components may not be separated by using frequency selective rf-pulses. The phase difference created during the time delay after the excitation pulse and before the detection of the MR signal may then be used to separate the two components. Phase sensitive imaging pulse sequence methods (Dixon, Radiology, 1984, 153: 189–194 and Sepponen, Mag Res. Imaging, 3, 163–167, 1985) may be used to generate images visualising different chemcial surroundings or different metabolites. The long $T_2$ relaxation time which may be a characteristic of a high $T_1$ agent will under these circumstances make it possible to use long echo times (TE) and still get a high signal-to-noise ratio. Thus an important advantage of the high $T_1$ agents used in the present method is that they exhibit a chemical shift dependent on the local composition of the body in which they are localized. Preferred high $T_1$ agents will exhibit at 1 T a chemical shift of more than 2 ppm, preferably more than 10 ppm depending on whether the high $T_1$ agent is localised inside or outside the vascular system. More preferred high $T_1$ agents will exhibit a chemical shift of more than 2 ppm, preferably more than 10 ppm, per 2 pH units or per Kelvin or upon being metabolised. High $T_1$ agents containing polarised $^{13}C$ nuclei (or $^{15}N$ nuclei) exhibit large changes in chemical shift in response to physiological changes (eg. pH, $pO_2$, $pCO_2$, redox potential, temperature or ionic concentrations of for example $Na^+$, $K'$, $Ca^{2+}$) or metabolic activity and therefore may be used to monitor these parameters.

Solid high $T_1$ agents (e.g. $^{13}C$ or $^{15}N$ enriched solids) may exhibit very long $T_1$ relaxation times and for this reason are especially preferred for use in the present method. The $T_1$ relaxation time may be several hours in the bulk phase, although this may be reduced by reduction of grain size and/or addition of paramagnetic impurities eg. molecular oxygen. The long relaxation time of solids advantageously allows the procedure to be conveniently carried out with less haste and is particularly advantageous in allowing the polarised solid high $T_1$ agent to be stored or transported prior to pharmaceutical formulation and administration. In one embodiment, the polarised high $T_1$ agent may be stored at low temperature and prior to administration, the high $T_1$ agent may be rapidly warmed to physiological temperatures using conventional techniques such as infrared or microwave radiation or simply by adding hot, sterile administrable media eg saline.

For in vivo use, a polarised solid high $T_1$ agent is dissolved in administrable media (eg water or saline), administered to a subject and conventional MR imaging performed. Thus solid high $T_1$ agents are preferably rapidly soluble (eg. water soluble) to assist in formulating administrable media. Preferably the high $T_1$ agent should dissolve in a physiologically tolerable carrier (eg water or Ringers solution) to a concentration of at least 1 mM at a rate of 1 mM/3 $T_1$ or more, particularly preferably 1 mM/2 $T_1$ or more, especially preferably 1 mM/$T_1$ or more. Where the solid high $T_1$ agent is frozen, the adminstrable medium may be heated, preferably to an extent such that the temperature of the medium after mixing is close to 37° C.

A polarised high $T_1$ agent may be administered (either alone or with additional components such as additional high $T_1$ agents) in liquid form. The retention of polarisation in a liquid medium vis-a-vis a gas medium is significantly greater. Thus while $T_1$ and $T_2$ are in general shorter for the liquid, the $T_2^*$ effect due to diffusion is $10^5$ times less significant for the liquid. Consequently for gaseous high $T_1$ agents the imaging sequence used generally has to be FLASH or GRASS while in contrast, more efficient imaging sequences may be used for liquids. For example, liquids generally have slower diffusion which makes it possible to use sequences such as echo planar imaging (EPI). The overall technique will be faster and yield better resolution (voxel size <1 mm) than conventional techniques (voxel size approx. 1–5 mm) at current acquisition times. It will give good images at all fields including in low field (eg. 0.01–0.5 T) machines.

Unless the hyperpolarised agent is stored (and/or transported) at low temperature and in an applied field as described above, since the method of the invention should be carried out within the time that the hyperpolarised solution of the high $T_1$ agent remains significantly polarised, it is desirable for administration of the polarised high $T_1$ agent to be effected rapidly and for the MR measurement to follow shortly thereafter. The preferred administration route for the polarised high $T_1$ agent is parenteral eg by bolus injection, by intravenous, intraarterial or peroral injection. The injection time should be equivalent to 5 $T_1$ or less, preferably 3 $T_1$ or less, particularly preferably $T_1$ or less, especially 0.1 $T_1$ or less. The lungs may be imaged by spray, eg by aerosol spray.

The high $T_1$ agent should be preferably enriched with nuclei (eg. $^{15}N$ and/or $^{13}C$ nuclei) having a long $T_1$ relaxation time. Preferred are $^{13}C$ enriched high $T_1$ agents having $^{13}C$ at one particular position (or more than one particular position) in an amount in excess of the natural abundance, i.e. above about 1%. Preferably such a single carbon position will have 5% or more $^{13}C$, particularly preferably 10% or more, especially preferably 25% or more, more especially preferably 50% or more, even more preferably in excess of 99% (e.g. 99.9%). The $^{13}C$ nuclei should preferably amount to >2% of all carbon atoms in the compound. The high $T_1$ agent is $^{13}C$ enriched at one or more carbonyl or quaternary carbon postions, given that a $^{13}C$ nucleus in a carbonyl group or in certain quaternary carbons may have a $T_1$ relaxation time typically of more than 2 s, preferably more than 5 s, especially preferably more than 30 s. Preferably the $^{13}C$ enriched compound should be deuterium labelled, especially adjacent the $^{13}C$ nucleus.

Viewed from a further aspect the present invention provides a composition comprising a hyperpolarised solution of a polarised $^{13}C$, $^{15}N$, $^{19}F$, $^{29}Si$, $^{31}P$ or $^1H$ enriched compound together with one or more physiologically acceptable carriers or excipients.

Viewed from a further aspect the present invention provides a contrast medium comprising a hyperpolarised solution of a polarised high $T_1$ agent being enriched with $^{13}C$, $^{15}N$, $^{19}F$, $^{29}Si$, $^{31}P$ or $^1H$ nuclei having a $T_1$ relaxation time of 2 s or more, preferably 10 secs or more, more preferably 30 secs or more, especially preferably 60 secs or more in solution at magnetic fields of 0.005–10 T, preferably 0.01–10 T, together with one or more physiologically acceptable carriers or excipients.

Preferred $^{13}C$ enriched compounds are those in which the $^{13}C$ nucleus is surrounded by one or more non-MR active nuclei such as O, S, C or a double bond. Specifically preferred $^{13}C$ enriched agents are $^{13}CO_3^{2-}$ and $H^{13}CO_3^-$ (sodium salt for injection and calcium or potassium salt for polarisation).

Also preferred are the following types of compound (* denotes $^{13}C$ enriched positions):

(1) carboxyl compounds comprising 1 to 4 carboxyl groups:

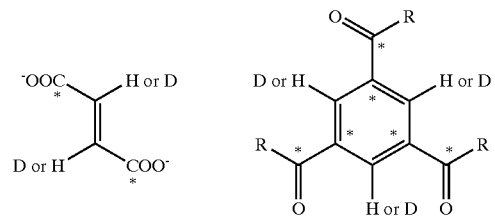

-continued

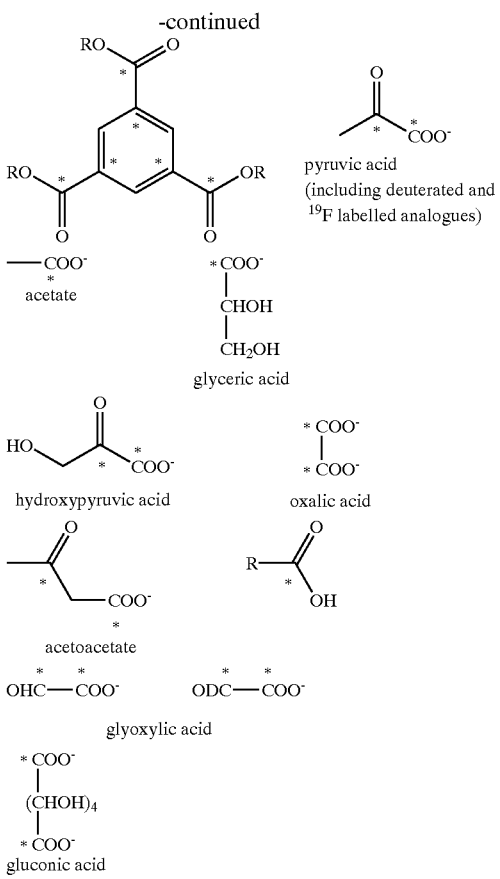

acetate pyruvic acid
(including deuterated and $^{19}$F labelled analogues)

glyceric acid hydroxypyruvic acid oxalic acid acetoacetate glyoxylic acid gluconic acid (wherein R represents any straight or branched chain hydrocarbon moiety, preferably a highly substituted carbon atom, especially preferably a quaternary carbon) and esters, isomers, especially stereoisomers and rotamers, thereof;

(2) substituted mono and biaryl compounds:

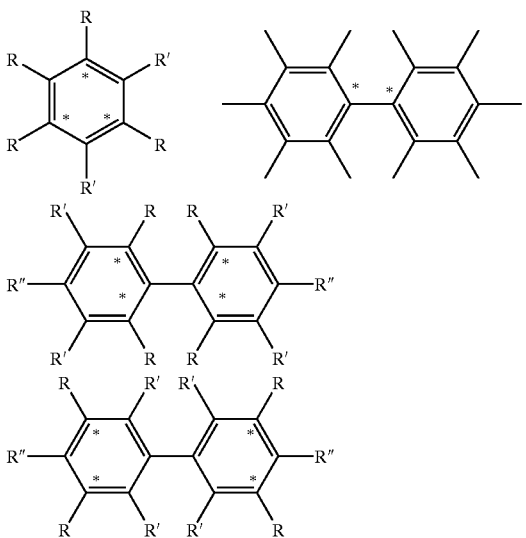

(wherein each group R or R' is independently a hydrogen atom, an iodine atom, a $^{19}$F atom or a hydrophilic moiety M being any of the non-ionizing groups conventionally used to enhance water solubility within the field of triiodophenyl X-ray contrast agents including for example a straight chain or branched $C_{1-10}$-alkyl group, preferably a $C_{1-5}$ group, optionally with one or more $CH_2$ or CH moieties replaced by oxygen or nitrogen atoms and optionally substituted by one or more groups selected from oxo, hydroxy, amino, carboxyl derivative, and oxo substituted sulphur and phosphorus atoms).

Particular examples of group M include polyhydroxyalkyl, hydroxyalkoxyalkyl and hydroxypolyalkoxyalkyl and such groups attached to the phenyl group via an amide linkage such as hydroxyalkylaminocarbonyl, N-alkyl-hydroxyalkylaminocarbonyl and bis-hydroxyalkylaminocarbonyl groups. Preferred among such M groups are those containing 1, 2, 3, 4, 5 or 6, especially 1, 2 or 3, hydroxy groups, e.g.

—$CONH—CH_2CH_2OH$

—$CONH—CH_2CHOHCH_2OH$

—$CONH—CH(CH_2OH)_2$

—$CON(CH_2CH_2OH)_2$ as well as other groups such as

—$CONH_2$

—$CONHCH_3$

—$OCOCH_3$

—$N(COCH_3)H$

—$N(COCH_3)C_{1-3}$-alkyl

—$N(COCH_3)$-mono, bis or tris-hydroxy $C_{1-4}$-alkyl

—$N(COCH_2OH)$-mono, bis or tris-hydroxy $C_{1-4}$-alkyl

—$N(COCH_2OH)_2$

—$CON(CH_2CHOHCH_2OH)(CH_2CH_2OH)$

—$CONH—C(CH_2OH)_3$ and

—$CONH—CH(CH_2OH)(CHOHCH_2OH)$.

In general, the M groups will preferably each comprise a polyhydroxy $C_{1-4}$-alkyl group, such as $C_{1-4}$-alkyl groups substituted by 1, 2, 3 or 4 hydroxy groups (e.g. hydroxymethyl, 2-hydroxyethyl, 2,3-bishydroxy-propyl, 1,3-bishydroxyprop-2-yl, 2,3,4-trihydroxybutyl, and 1,2,4-trihydroxybut-2-yl) optionally connected to the phenyl ring via a CO, SO or $SO_2$ group (e.g. $COCH_2OH$ or $SO_2CH_2OH$).

Preferred compounds are those in which two or three non-adjacent R groups in the or each $C_6R_5$ moiety are iodine and at least one, and preferably two or three, R groups in the or each $C_6R_5$ moiety are M or $M_1$ moieties; each M independently is a non-ionic hydrophilic moiety; and each $M_1$ independently represents a $C_{1-4}$-alkyl group substituted by at least one hydroxyl group and optionally linked to the phenyl ring via a carbonyl, sulphone or sulphoxide group, at least one 2 group, preferably at least two R groups and especially preferably at least one R group in the or each $C_6R_5$ moiety, being an $M_1$ moiety. Especially preferred are the compounds disclosed in WO-A-96/09282.

(3) sugars:

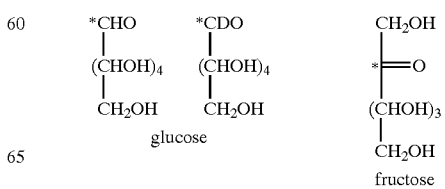

glucose fructose

-continued

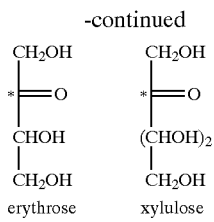
erythrose    xylulose

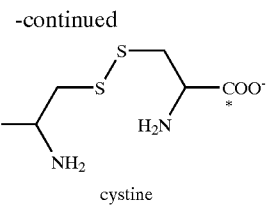
cystine (4) ketones:

(wherein R and R' are as defined above)

(5) ureas:

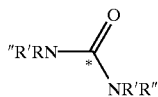 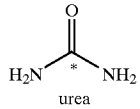
urea (6) amides:

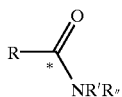

(7) amino acids:

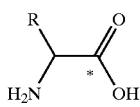

and peptides and proteins labelled in the carbonyl position, particularly those known in the art to be useful for targetting tumour cells. Of the proteins, albumin is especially preferred. Polymers are also useful, particularly those with low toxicity (eg, polylysine) and those with many carboxyl groups (eg polyglutamic acid). The following amino acids are especially preferred:

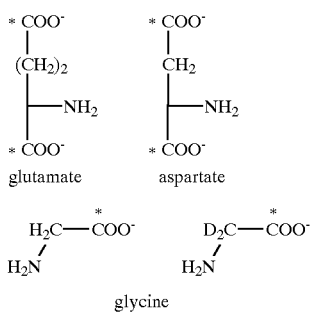
glutamate    aspartate glycine (8) carbonates:

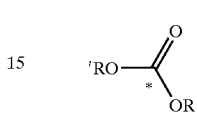

(9) nucleotides:

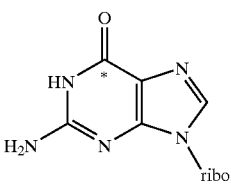 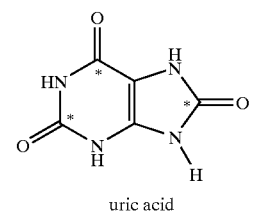
guanylic acid    uric acid

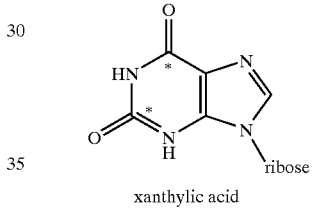
xanthylic acid

(10) tracers:

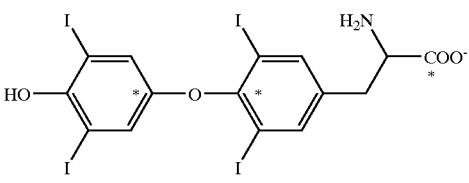
thyroxine

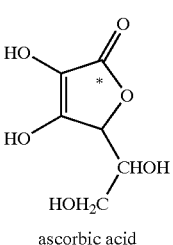
ascorbic acid

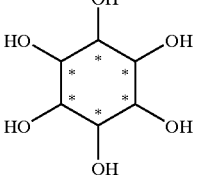
inositol

-continued
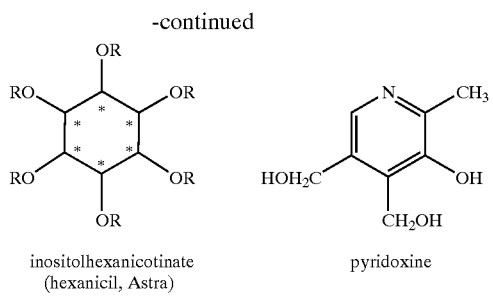
inositolhexanicotinate
(hexanicil, Astra)
pyridoxine
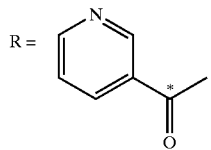
cinoxazin
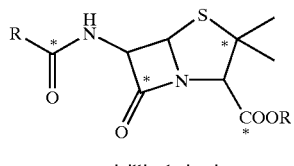
penicillin derivatives
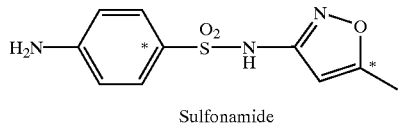
Sulfonamide
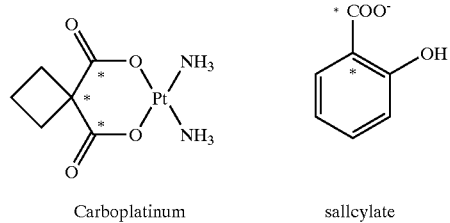
Carboplatinum    salicylate
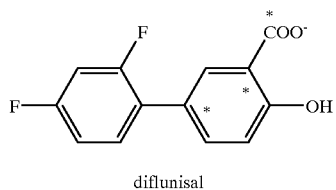
diflunisal
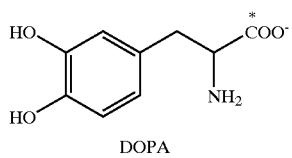
DOPA
and
(11) compounds such as:
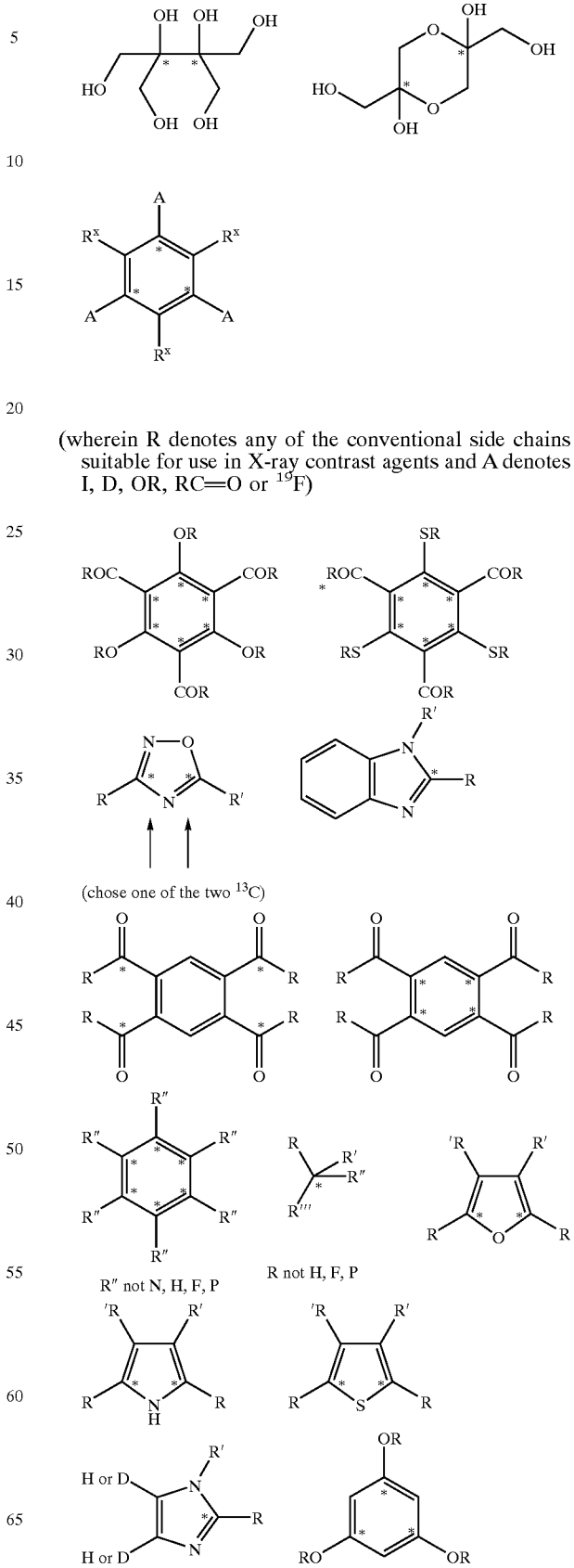
(wherein R denotes any of the conventional side chains suitable for use in X-ray contrast agents and A denotes I, D, OR, RC=O or $^{19}F$)
(chose one of the two $^{13}C$)
R″ not N, H, F, P    R not H, F, P

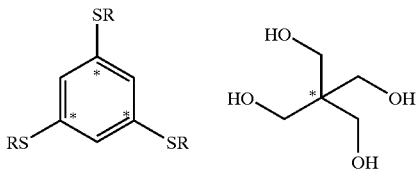

In any of the above definitions, unless otherwise specified R, R', R" and R'" denote any suitable substituent, preferably a substituent bound by a non-magnetic nucleus.

The partly or wholly deuterated or $^{14}F$ analogues of any of these compounds are particularly preferred.

Certain of the above-mentioned $^{13}C$ enriched compounds are novel per se and form a further aspect of the invention. Compounds which are water soluble are particularly preferred.

In general, $^{13}C$ enriched amino acids and any known contrast agents from the fields of X-ray contrast agents and MRI contrast agents (the chelating agent without the metal counterion eg conventional Gd chelating agents without Gd) are preferred as high $T_1$ agents Intermediates in normal metabolic cycles such as the citric acid cycle eg. fumaric acid and pyruvic acid are preferred for the imaging of metabolic activity.

$T_1$ values for $^{13}C$ enriched compounds useful in the invention are reported in the literature or may be routinely determined. Examples include:

(a) non-water soluble (i.e soluble in an organic solvent)

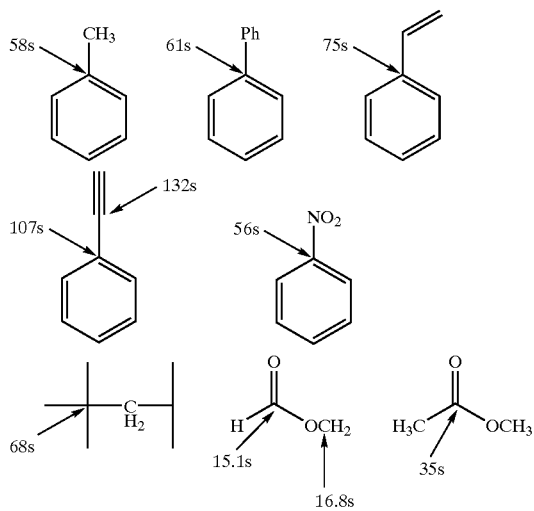

(b) water soluble

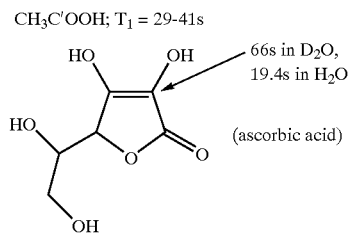

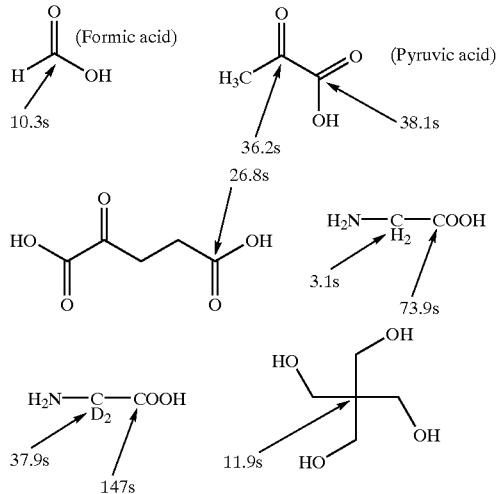

Hyperpolarisation may be carried out by any known method and by way of example three such methods are described hereinbelow. It is envisaged that, in the method according to the invention, the level of polarisation achieved should be sufficient to allow the hyperpolarised solution of the high $T_1$ agent to achieve a diagnostically effective contrast enhancement in the sample to which it is subsequently administered in whatever form In general, it is desirable to achieve a level of polarisation which is at least a factor of 2 or more above the field in which MRI is performed, preferably a factor of 10 or more, particularly preferably 100 or more and especially preferably 1000 or more, eg. 50000.

In a first embodiment of the method according to the invention, hyperpolarisation of the MR imaging nuclei is effected by an OMRI contrast agent. In this embodiment, step (i) of the method comprises:

(a) bringing an OMRI contrast agent and a high $T_1$ agent into contact in a uniform magnetic field (the primary magnetic field $B_o$);

(b) exposing said OMRI contrast agent to a first radiation of a frequency selected to excite electron spin transitions in said OMRI contrast agent; and (c) dissolving in a physiologically tolerable solvent said high $T_1$ agent. It is preferred that the OMRI contrast agent and high $T_1$ agent are present as a composition during polarisation.

Dynamic nuclear polarisation may be attained by three possible mechanisms: (1) the Overhauser effect, (2) the solid effect and (3) thermal mixing effect (see A. Abragam and M. Goldman, Nuclear Magnetism: order and disorder, Oxford University Press, 1982). The Overhauser effect is a relaxation driven process that occurs when the electron-nucleus interaction is time-dependent (due to thermal motion or relaxation effects) on the time scale of the inverse electron Larmor frequency or shorter. Electron-nuclear cross-relaxation results in an exchange of energy with the lattice giving rise to an enhanced nuclear polarisation. The overall enhancement depends on the relative strength of the scalar and dipolar electron-nuclear interaction and the microwave power. For static systems both thermal mixing and the solid effect are operative. In the solid effect, the electron spin system is irradiated at a frequency that corresponds to the sum or difference of the electronic and nuclear Larmor frequencies. The nuclear Zeeman reservoir absorbs or emits the energy difference and its spin temperature is modified, resulting in an enhanced nuclear polarisation. The efficiency depends on the transition probabilities of otherwise forbidden transitions that are allowed due to the mixing of nuclear states by non-secular terms of the electron-nuclear dipolar interaction. Thermal mixing arises when the electron-electron dipolar reservoir establishes thermal contact with the nuclear Zeeman reservoir. This takes place when the characteristic electronic resonance line width is of the order of the nuclear Larmor frequency. Electron-electron cross relaxation between spins with difference in energy equal to the nuclear Zeeman energy is absorbed or emitted by the electronic dipolar reservoir, changing its spin temperature and the nuclear polarisation is enhanced. For thermal mixing both the forbidden and the allowed transitions can be involved.

In the first embodiment where the polarising agent is an OMRI contrast agent, the method may be conveniently carried out by using a first magnet for providing the polarising magnetic field and a second magnet for providing the primary magnetic field for MR imaging. The same magnet could be used for both purposes. FIG. 1 of the accompanying drawings is a schematic representation of an apparatus suitable for carrying out the first embodiment of the invention. A freestanding polarising magnet (1) optionally together with a filter surrounds an EPR resonator (2) which provides the nuclear polarisation. A container (3) comprising a pump is provided for carrying the contrast composition which is delivered to a subject (4) by a delivery line (5). The subject is situated within a conventional MR scanner (6).

In the above apparatus, a dielectric resonator may be used in the dynamic nuclear polarisation process. Generally speaking, dynamic nuclear polarisation requires a volume with a fairly strong high frequency magnetic field and an accompanying electric field which is made as small as possible. A dielectric resonator may be used to provide a preferred field arrangement in which the magnetic field lines are shaped like a straw in a sheaf of corn with an electric field forming circles like the thread binding the sheaf. A field arrangement of this type may be formed by one of several rings or tubes of a material with a high dielectric constant and low loss. The man skilled in the art will appreciate that such a tube will exhibit different electromagnetic resonant modes. One of the dominant modes has the desired characteristic of electric field circulating around the tube axis within the wall and being zero at the axis and everywhere perpendicular to it. The magnetic field on the other hand is concentrated around the tube axis and mainly directed along it. The composition to be polarised is conveniently placed inside the resonator which is itself placed inside a metal box with a clearance typically of the order of the size of the resonator, and is excited to the desired resonance with a coupling loop or the like. The metal box ensures that the electromagnetic energy does not leak away by radiation. FIG. 2 of the accompanying drawings shows a dielectric resonator (1) (with an axis of rotational symmetry (2)) within a metal box (3).

An alternative to the dielectric resonator is a resonant cavity of which several are known to those skilled in the art. One simple and efficient resonant cavity is a metal box, such as a cylindrical metal box. A suitable mode is the one known as TM1,1,0 which produces a perpendicular magnetic field on the axis of the cavity. It is possible to excite two such modes in the same cavity at the same frequency producing fields which are mutually perpendicular. By arranging them to have a 90° phase difference a rotating field can be produced which is especially efficient for implementing dynamic polarisation with a minimum of dissipation in the sample. Modes with similar field distributions for different shapes of cavities e.g. rectangular cavities are familiar to those skilled in the art.

The composition may also be dispersed into a plurality of compartments during the dynamic nuclear polarisation step. Thus the composition might be typically divided into parallel channels provided, for example, by parallel separating plates, discs or tubes, typically open-ended tubes. The electric losses (eddy currents) in the composition caused by the magnetic field are decreased by dividing the composition into smaller volumes using electrically isolating barriers, preferably situated perpendicular to the field. If the composition is in a cylindrical vessel surrounded by a dielectric resonator as described hereinbefore, the isolating barriers would be planes passing radially from the vessel axis to its wall. A simpler and more practical arrangement is to polarise the composition in a container which contains a plurality of thin-walled tubes of an isolating material such as quartz, glass or plastic. This has the advantage of reducing the electric losses in the composition which allows a larger volume of composition to be polarised for the same applied electromagnetic power. The walls, the inner, outer or both of the tubes may similarly serve as the substrate onto which the OMRI contrast agent is bound so that pressure applied to one end of the container may force the polarized, substantially OMRI contrast agent free, fluid high $T_1$ agent from the container, for example with a delivery line leading to the subject (patient) undergoing MR examination.

It is envisaged that in the first embodiment of the method according to the invention, use may be made of any known OMRI contrast agent capable of polarising a high $T_1$ agent to an extent such that a diagnostically effective contrast enhancement, in the sample to which the high $T_1$ agent is administered, is achieved. Where the OMRI contrast agent is a paramagnetic free radical, the radical may be conveniently prepared in situ from a stable radical precursor by a conventional physical or chemical radical generation step shortly before polarisation, or alternatively by the use of ionising radiation. This is particularly important where the radical has a short half-life. In these cases, the radical will normally be non-reusable and may conveniently be discarded once the separation step of the method according to the invention has been completed.

In solids, it is preferred to effect dynamic nuclear polarisation by irradiating an electron spin at low temperature and high field. Specific examples of dynamic nuclear polarisation of solid high $T_1$ agents are:

(1) 15N-Ala labelled T4-lysosome and 13C-Glycine in frozen aqueous solutions of 60:40 glycerol/water with the free radical 4-amino TEMPO as the source of electron polarisation (D. A. Hall, D. Maus, G. Gerfen and R. G. Griffin, Science, 1997), Enhancements of ca. 50 and 100 were obtained, respectively, at 5 T and 40 K;

(2) Carboxy-13C labelled glycine in frozen aqueous solution of 60:40 glycerol/water with TEMPO as the free radical. An enhancement of 185 at 5 T and 14 K was obtained (G. J. Gerfen, L. R. Becerra, D. A. Hall, R. G. Griffin, R. J. Temkin, D. J. Singel, J. Chem. Phys. 102(24), 9494–9497 (1995);

(3) Dynamic polarisation of protons and deuterons in 1,2-ethanediol doped with complexes of Cr at 2.5 T. The obtained degree of polarisation is 80% (W. De Boer and T. O Niinikoski, Nucl. Instrum. Meth. 114, 495 (1974).

Preferably of course a chosen OMRI contrast agent will exhibit a long half-life (preferably at least one hour), long relaxation times ($T_{1e}$ and $T_{2e}$), high relaxivity and a small number of ESR transition lines. Thus the paramagnetic oxygen-based, sulphur-based or carbon-based organic free radicals or magnetic particles referred to in WO-A-88/10419, WO-A-90/00904, WO-A-91/12024, WO-A-93/02711 or WO-A-96/39367 would be suitable OMRI contrast agents.

However, OMRI contrast agents useful in the first embodiment of the present method are not limited to paramagnetic organic free radicals. Particles exhibiting the magnetic properties of paramagnetism, superparamagnetism, ferromagnetism or ferrimagnetism may also be useful OMRI contrast agents, as may be other particles having associated free electrons. Superparamagnetic nanoparticles (eg. iron or iron oxide nanoparticles) may be particularly useful. Magnetic particles have the advantages over organic free radicals of high stability and a strong electronic/nuclear spin coupling (i.e. high relaxivity) leading to greater Overhauser enhancement factors.

For the purposes of administration, the high $T_1$ agent should be preferably administered in the absence of the whole of, or substantially the whole of, the OMRI contrast agent. Preferably at least 80% of the OMRI contrast agent is removed, particularly preferably 90% or more, especially preferably 95% or more, most especially 99% or more. In general, it is desirable to remove as much OMRI contrast agent as possible prior to administration to improve physiological tolerability and to increase $T_1$. Thus preferred OMRI contrast agents for use in the first embodiment of the method according to the invention are those which can be conveniently and rapidly separated from the polarised high $T_1$ MR imaging agent using known techniques as discussed below. However where the OMRI contrast agent is nontoxic, the separation step may be omitted. A solid (eg. frozen) composition comprising an OMRI contrast agent and a high $T_1$ agent which has been subjected to polarisation may be rapidly dissolved in saline (eg. warm saline) and the mixture injected shortly thereafter.

In the separation step of the first embodiment of the method of the invention, it is desirable to remove substantially the whole of the OMRI contrast agent from the composition (or at least to reduce it to physiologically tolerable levels) as rapidly as possible. Many physical and chemical separation or extraction techniques are known in the art and may be employed to effect rapid and efficient separation of the OMRI contrast agent and high $T_1$ agent. Clearly the more preferred separation techniques are those which can be effected rapidly and particularly those which allow separation in less than one second. In this respect, magnetic particles (eg. superparamagnetic particles) may be advantageously used as the OMRI contrast agent as it will be possible to make use of the inherent magnetic properties of the particles to achieve rapid separation by known techniques. Similarly, where the OMRI contrast agent or the particle is bound to a solid bead, it may be conveniently separated from the liquid (i.e. if the solid bead is magnetic by an appropriately applied magnetic field).

For ease of separation of the OMRI contrast agent and the high $T_1$ agent, it is particularly preferred that the combination of the two be a heterogeneous system, eg. a two phase liquid, a solid in liquid suspension or a relatively high surface area solid substrate within a liquid, eg. a solid in the form of beads fibres or sheets disposed within a liquid phase high $T_1$ agent. In all cases, the diffusion distance between the high $T_1$ agent and OMRI contrast agent must be small enough to achieve an effective Overhauser enhancement. Certain OMRI contrast agents are inherently particulate in nature, eg. the paramagnetic particles and superparamagnetic agents referred to above. Others may be immobilized on, absorbed in or coupled to a solid substrate or support (eg. an organic polymer or inorganic matrix such as a zeolite or a silicon material) by conventional means. Strong covalent binding between OMRI contrast agent and solid substrate or support will, in general, limit the effectiveness of the agent in achieving the desired Overhauser effect and so it is preferred that the binding, if any, between the OMRI contrast agent and the solid support or substrate is weak so that the OMRI contrast agent is still capable of free rotation. The OMRI contrast agent may be bound to a water insoluble substrate/support prior to the polarisation or the OMRI contrast agent may be attached/bound to the substrate/support after polarisation. The OMRI contrast agent may then be separated from the high $T_1$ agent e.g. by filtration before administration. The OMRI contrast agent may also be bound to a water soluble macromolecule and the OMRI contrast agent-macromolecule may be separated from the high $T_1$ agent before administration.

Where the combination of an OMRI contrast agent and high $T_1$ agent is a heterogeneous system, it will be possible to use the different physical properties of the phases to carry out separation by conventional techniques. For example, where one phase is aqueous and the other non-aqueous (solid or liquid) it may be possible to simply decant one phase from the other. Alternatively, where the OMRI contrast agent is a solid or solid substrate (eg. a bead) suspended in a liquid high $T_1$ agent the solid may be separated from the liquid by conventional means eg. filtration, gravimetric, chromatographic or centrifugal means. It is also envisaged that the OMRI contrast agents may comprise lipophilic moieties and so be separated from the high $T_1$ agent by passage over or through a fixed lipophilic medium or the OMRI contrast agent may be chemically bound to a lipophilic solid bead. The high $T_1$ agent may also be in a solid (eg. frozen) state during polarisation and in close contact with a solid OMRI contrast agent. After polarisation it may be dissolved in heated water or saline or melted and removed or separated from the OMRI contrast agent where the latter may be toxic and cannot be administered.

One separation technique makes use of a cation exchange polymer and a cationic OMRI contrast agent, eg. a triarylmethyl radical carrying pendant carboxylate groups. Alternatively acidifying the solution to around pH 4 may cause the OMRI contrast agent to precipitate out. Separation may then be carried out for example by filtration followed by neutralisation. An alternative technique involves adding ions which causes precipitation of ionic OMRI agents which may then be filtered off.

Certain OMRI contrast agents, such as the triarylmethyl radical, may have an affinity for proteins. Thus, after polarisation, a composition containing an OMRI contrast agent with a protein affinity may be passed through or over a protein in a form which exposes a large surface area to the agent eg. in particulate or surface bound form. In this way, binding of the OMRI contrast agent to the protein enables it to be removed from the composition.

Alternatively when a hydrophilic high $T_1$ agent is in a solid (eg. frozen) form it may be brought into contact with a hydrophobic OMRI contrast agent which is dissolved in an organic fluid with a melting temperature higher than the high $T_1$ agent. The mixture is frozen and polarisation performed. After polarisation, the mixture is heated and the solid OMRI contrast agent and its solvent are removed. The high $T_1$ agent will remain hyperpolarised for a significant time in the frozen state and may be transported long distances before being dissolved in water or saline for injection.

In a second embodiment of the method according to the invention, hyperpolarisation of the nuclei is effected by a hyperpolarisable gas. In this second embodiment, step (i) of the method according to the invention comprises:

(a) hyperpolarising a hyperpolarisable gas before, during or after introducing a high $T_1$ agent thereto whereby to cause nuclear polarization of said high $T_1$ agent;

(b) dissolving in a physiologically tolerable solvent said high $T_1$ agent, and wherein said high $T_1$ agent is not limited to $^{13}C$ enriched agents at one or more carbonyl or quaternary carbon positions By hyperpolarisable gas is meant a gas with a non-zero spin angular momentum capable of undergoing an electron transition to an excited electron state and thereafter of decaying back to the ground state.

Depending on the transition that is optically pumped and the helicity of the light a positive or negative spin hyperpolarisation may be achieved (up to 100%). Examples of gases suitable for use in the second embodiment of the method of the invention include the noble gases He (eg. $^3$He or $^4$He) and Xe (eg. $^{129}$Xe) preferably He, particularly preferably $^3$He. Alkali metal vapours may also be used eg. Na, K, Rb, Cs vapours. Mixtures of the gases may also be used or the hyperolarisable gas may be used in liquid or solid form. The term hyperpolarisable gas also covers any gas with non-zero nuclear spin which may be polarised by optical pumping and is preferably $^{129}$Xe or $^3$He.

It will be appreciated that in the second embodiment of the invention, the hyperpolarised gas may transfer polarisation to the nuclear spin system of a high $T_1$ agent directly or indirectly. Where the high $T_1$ agent is to be polarised indirectly by water vapour, it may be advantageously water soluble.

For the purposes of polarisation according to the second embodiment of the invention, the high $T_1$ agent may be generally in gaseous, liquid or solid form.

Where the high $T_1$ agent is polarised whilst in a gaseous state, it is convenient (for the purposes of separation from the hyperpolarised gas and of administration) to be able to rapidly convert it into a liquid or solid. This has the added benefit of significantly increasing $T_1$. Thus removing the elevated pressure and temperature imposed on the gas mixture will lead to rapid cooling and condensation. Yet further cooling is possible by, for example, contacting the polarised high $T_1$ agent with a cold surface.

In a preferred embodiment, a hyperpolarised fluid eg. $^{129}$Xe at elevated pressure and/or low temperature is passed through a column of solid $^{13}C$ enriched and/or $^{19}F$ enriched high $T_1$ agent until steady state polarisation of the solid is almost achieved. In general any of the above-mentioned $^{19}C$ enriched agents may be used.

In another preferred embodiment, a hyperpolarised gas is frozen/crystallised on the solid/frozen surface of a solid high $T_1$ agent which has been prepared with as large a surface area as possible. The mixture may be transported before warm administrable media (eg. saline) is added and physiological temperature reached before injection.

$^{129}$Xe gas can be produced in a highly spin polarised state in macroscopic quantities. Due to the limited solubility and inert nature of xenon there is interest in transferring the polarisation to other nuclei.

It can also be produced by irradiating a polarising agent, e.g. with an electron spin resonance transition stimulating radiation (e.g. microwave radiation). This forms a further aspect of the invention. Viewed from this aspect the invention provides a method of magnetic resonance investigation of a sample, preferably of a human or non-human animal body, said method comprising:

i) producing solid hyperpolarised $^{129}$Xe by irradiating a polarising agent whereby to cause dynamic nuclear polarisation.

In the above method said polarising agent is preferably a substance containing an unpaired electron, for example nitroxide, trityl, Cr(V), or the OMRI agents mentioned above.

Considerable interest has been generated in the novel technique of MR lung imaging using hyperpolarised gases such as $^3$He and $^{129}$Xe as inhaled contrast media. However, the production of these gases in their hyperpolarised form is labourious and time consuming. At the present time, $^3$He, where most of the interest is today, can be generated at a rate of a few liters an hour. However, if the hyperpolarisation could be done in the liquid or solid phase, much higher production rates would be possible. Using only "brute force", i.e. milliKelvin temperatures and >10 T, fields would be an extremely costly method, however, "double brute force", i.e. irradiation of frozen Xe in the presence of a free radical (metal ion, trityl radical, nitroxide, etc.) at a comparatively moderate temperature (a few K) would be a more practical method. The radical would be added either in pure form or bound to a matrix. After the irradiation had been carried out, heating of the sample would release the hyperpolarised gas and a new batch of Xe could be condensed and irradiated. Since the hyperpolarisation in this case is carried out on solid Xe, the possibilities of producing large amounts of gas would be considerable.

The main relaxation mechanism for solid $^{129}$Xe is spin exchange with the rapidly relaxing $^{131}$Xe, the major component in natural xenon. The magnetogyric ratio of $^{129}$Xe and $^{131}$Xe differs by a factor of four. Normally the line widths of the resonances of solids are on the order of a few kHz. When the difference in Larmor frequency is on the same order as the line width, the polarisation of the nuclei will rapidly equilibrate. Assuming that we have a cold (colder than the freezing point of xenon, around 150 K, depending on the pressure), finely divided (some micrometers grain size), sample of a $^{13}C$ labelled substance with a long $T_1$ in the solid and allow hyperpolarised xenon to form frost on the powder. If this operation is performed in a magnetic field of suitable strength the $^{129}$Xe and the 13C will overlap and Xe-C spin flip-flops will be efficient, equilibrating the polarisation between xenon and carbon. The xenon can then be pumped off and the process repeated until a suitable level of polarisation is achieved. What the suitable field strength is depends on the exact lineshapes but assuming line widths on the order of 5–10 kHz, which is quite normal for solids, the optimum field is around 10 mT, typically the field on the outside of an NMR-magnet or a small toy magnet. The basis for this is that the centre frequency of the line is field dependent whereas the linewidth is essentially independent of the field.

FIG. 3 shows the behaviour of such a system at various field strengths. One important factor to take into account is that all the nuclei in the sample must be taken into consideration. This method will work for transfer from $^{129}$Xe to $^{13}C$ and possibly to $^{29}$Si but it is not expected to work with $^{19}N$ which has a resonance frequency that is closer to $^{131}$Xe than to $^{129}$Xe. There will be interference from quadrupolar nuclei like $^{23}$Na, $^{79}$Br, $^{81}$Br, $^{127}$I and a number of transition metals, all having resonance frequencies similar to carbon.

In order to generate a hyperpolarised gas, the gas is first subjected to a discharge or other means of excitation (eg. an appropriate radiofrequency) which creates a metastable unpaired electron spin state and is then optically (eg. laser) pumped at an appropriate frequency to create electron hyperpolarisation. The various methods for achieving this are well known to those skilled in the art or are described in inter alia U.S. Pat. No. 5545396.

Preferred hyperpolarisable gases for use in the second embodiment of the method according to the invention are those which can be conveniently and rapidly separated from the polarised high $T_1$ agent. Noble gases are particularly useful given their very low boiling points and inertness. Preferably the chosen gas will exhibit a long hyperpolarisability half-life (preferably at least 1000 s, particularly preferably at least 4000 s and especially preferably 8000 s or more).

A hyperpolarised gas may, if desired, be stored for extended periods of time in a hyperpolarised state. This is achieved by maintaining the gas at very low temperatures, preferably in a frozen state.

For ease of separation of the hyperpolarisable gas and the high $T_1$ agent, the combination of the two may be advantageously a heterogeneous system, eg. the high $T_1$ agent is a solid at ambient temperatures. In all cases, the diffusion distance between the high $T_1$ agent and gas, fluid or solid must be small enough to achieve an effective polarisation.

In the separation step of the second embodiment of the method of the invention, it is desirable to remove substantially the whole of the hyperpolarisable gas from the composition (or at least to reduce it to physiologically tolerable levels) as rapidly as possible. If desired, the gas may be reused which may be an important consideration given the expense of noble gases. Many physical and chemical separation or extraction techniques known in the art may be employed to effect rapid and efficient separation of the hyperpolarisable gas and high $T_1$ agent. Clearly the more preferred separation techniques are those which can be effected rapidly and particularly those which allow separation in a fraction of the relaxation time $T_1$ of the high $T_1$ agent.

In a third embodiment of the method of the invention, hyperpolarisation of the MR imaging nuclei is effected by the use of a high field as described in U.S. Pat. No. 5,479,925 (GEC) and U.S. Pat. No. 5,617,859 (GEC). U.S. Pat. No. 5,479,925 discloses a method for generating MR angiograms in which a contrast agent is passed through a small, high field polarising magnet ex vivo, in order to generate a high longitudinal magnetisation in the agent prior to its administration to the subject. There is however no mention or suggestion of the use of high $T_1$ agents to achieve an improved effect.

Generally speaking, polarisation of an MR imaging nuclei may be achieved by thermodynamic equilibration at low temperature and high magnetic field. Where the contrast medium to be administered is a solid material (e.g. crystalline), it may be introduced into a magnetic field at very low temperature. Under these conditions, $T_1$ is very long (typically many hours or months) and consequently it takes an unacceptably long time for the medium to reach thermodynamic equilibrium. Thus if the contrast medium undergoes small movements in the gradient field for example by exposure to a magnetic field gradient and ultrasound or by relative movement within the gradient field, $T_1$ will drop. When thermodynamic equilibrium is attained, all nuclei in the contrast medium will be highly polarised relative to room temperature and to normal magnetic fields used in MRI. This procedure has the advantage of allowing the contrast medium to be removed from the magnet and transported in a "ready-to-use" form to the place where it is to be used. Preferably but not essentially transport may take place at a relatively low temperature (e.g. at liquid nitrogen temperature). The $T_1$ of the high $T_1$ solid contrast medium will be long enough to allow transport at ambient temperature before use.

One of the main obstacles in using so-called 'brute force' polarisation as a method for hyperpolarising samples are the long $T_1$ values at low temperatures and high fields, typically several weeks at temperatures below 1 K. However it has been found that it is possible to utilise the non-linear field dependence of $T_1$ to shorten the time necessary for relaxation by a gradual increase of the external magnetic field.

As stated above, it is of great interest to obtain hyperpolarised injectable contrast agents. Theoretically, the simplest way of obtaining a highly spin-polarised material is to cool it to a very low temperature in a strong magnetic field and let the sample reach thermal equilibrium. The major practical problem in using this technique is the time required for the thermal equilibration to occur. At temperatures below 1 K the time constant for that process, $T_1$, might be on the order of weeks.

The time constant of nuclear longitudinal relaxation, $T_1$, shows a quadratic dependence on the field strength in solid materials:

$$T_1 = T_{1,0} + cB$$

Where $T_{1,0}$ is the time constant for relaxation at no external magnetic field, c is a constant, and B is the external magnetic field.

The rate of magnetisation of the sample, dM/dt, at a given field strength will then be given by:

$$dM/dt = (M_{max} - M)/T_1$$

Where $M_{max}$ is the magnetisation of the sample after complete relaxation at the final field. Since the field-dependence of the time constant is non-linear, it will be possible to obtain a larger magnetisation at a given time by constantly tuning the external magnetic field so that the rate of magnetisation all the time is as big as possible. The example shown in attached FIGS. 4 and 5 was chosen to simulate the behaviour of the carbonyl carbon in solid sodium acetate. The $T_1$ at 7 T is 1700 seconds and the $T_{1,0}$ is about 5 seconds. The time to reach the same degree of magnetisation as after 1700 seconds at a constant field of 7 T, is reduced to 1390 seconds, a reduction of almost 20%, which could easily reduce the equilibration time by one week at milliKelvin temperatures. The optimised field-ramp is shown in FIG. 4, whilst FIG. 5 shows the expected values from a numerical integration of the equation for dM/dt given above. This process will be applicable for all nuclei with spin but will be most interesting with compounds with long $T_1$ values As stated above, one of the main obstacles in using so-called 'brute force' polarisation as a method for hyperpolarising samples is the long $T_1$ values found at low temperatures and high fields, typically several weeks at temperatures below 1 K. It is possible to use the technique of low-field matching to increase the relaxation rate and the degree of polarisation of the nuclear spins in solids at low temperature. This has the additional advantage that a brute force polariser does not need to possess any radio frequency electronics.

It is well known that different nuclei in the same molecule will relax with different time constants. A way of speeding up the polarisation of the interesting $^{13}C$ nucleus and at the same time obtaining a better polarisation is to use cross-polarisation from the quickly relaxing proton to the slowly relaxing carbon, a method routinely used in solid-state NMR spectroscopy. Due to the big difference in magnetogyric ratio between the proton and $^{13}$C, the energy difference is large and hence the polarisation transfer slow. The magnetogyric ratio of the proton is roughly a factor of four larger than that of carbon. The situation can be improved by utilising the procedure of spin locking under Hartman-Hahn conditions. Spin-lock ($90_x$-long pulse,) at both nuclei with the amplitude ($B_1$) of the long pulse satisfying the Hartman-Hahn condition:

$$\gamma H B_{1H} = \gamma C B_{1C}$$

where $\gamma H$ is the magnetogyric ratio of hydrogen, $\gamma C$ is the magnetogyric ratio of carbon, $B_{1H}$ is the proton excitation field and $B_{1C}$ is the carbon excitation field.

This allows for mutually matched flip-flops of the spins. Since this is a spin-spin process, it usually occurs on time scales from about 100 µs to a few ms.

One problem with this is that radiofrequency electronics are required and furthermore the homogeneity of the magnetic field must be high enough to allow precise pulse angles. A way to circumvent this problem is the following.

A crude way of stating the Hartman-Hahn condition is to say that spin diffusion is efficient when the resonance lines of the two nuclei overlap. Assume the substrate to be a solid material with a half-height line width of 5 kHz. This linewidth is caused by dipolar coupling and is independent of the external field. The Hartman-Hahn condition is now restated as follows. Efficient spin-diffusion takes place when the maxima of the two resonances are separated by less than the sum of their half-height line-widths. The field where this condition is fulfilled is derived as follows.

The resonance frequency, v is given by:

$$v = \gamma B_0 / 2\pi \quad (1)$$

where $\gamma$ is the magnetogyric ratio, and $B_0$ is the external magnetic field. The required separation, v, was 5 kHz:

$$v = v_H - v_C = 5000 \; s^{-1} \quad (2)$$

Combination of equation (1) and (2) gives:

$$v = B_0(\gamma_H - \gamma_C)/2\pi$$

which can be rewritten as:

$$B_0 = v 2\pi/(\gamma_H - \gamma_C) = 156 \; \mu T$$

This field is within a factor 3 of the earth's magnetic field which means that if the sample is removed from the polarising magnet for a few seconds the polarisation will equilibrate between carbon and hydrogen on a time scale similar to $T_2$ so there will be plenty of time to put the sample back into the magnet again before the $T_1$ relaxation becomes significant, even if it has to be kept in mind that the $T_1$ shortens dramatically for solids in low fields. It will, however, never be as short as the $T_2$.

This procedure can be repeated after the protons have repolarised again, successively building up the carbon polarisation until the spin-temperature of the two nuclei become the same. The protons in solid sodium acetate has, at room temperature, a $T_1$ of 31 s whilst the $T_1$ of the carbonyl carbon in the same sample is 1700 s. If this difference could be used completely there would be a shortening of the polarisation time by a factor of 55. Generally fluorine relaxes even faster than protons and it would be possible to include a fluorine atom in the contrast agent molecule as an internal relaxation agent.

It is also possible to use quadrupolar nuclei for this process. The sodium ions in solid sodium acetate have a $T_1$ of 1.7 s at room temperature. Sodium has a magnetogyric ratio only slightly higher than carbon which means that equilibration occurs at a much higher field, in this case at 8.9 mT, a field found about 15 cm above the Dewar of a 7 T NMR magnet. This is of great help for rapid polarisation of samples at low temperature, but is also a problem in the storage of polarised samples. The magnetic storage field must be large enough to avoid overlap of the resonances of the wanted nucleus and any rapidly relaxing quadrupolar nuclei. It is known that this phenomenon causes the rapid relaxation of frozen $^{129}$Xe in a low field, when spin diffusion to the quadrupolar $^{131}$Xe becomes efficient.

There is also the possibility of transferring polarisation from unpaired electrons to carbon. Due to the great difference in magnetogyric ratios this requires a field much lower than the earth magnetic field to become efficient. Such a low field requires that the sample be moved to a magnetically shielded area. One way of achieving this is to have a small magnet with opposite polarity some distance along the polarity axis of the main coil. With careful design the fields can be made to cancel in the centre of the small magnet.

The magnetic field strength used in this third embodiment of the invention should be as high as possible, preferably >1 T, more preferably 5 T or more, especially preferably 15 T or more. The temperature should be very low e.g. 100 K or less, preferably 4.2 K or less, more preferably 1 K or less, even more preferably 0.1 K or less, especially preferably 1 mK or less.

Thus viewed from a further aspect the present invention provides a method for preparing polarised high $T_1$ agents, said method comprising the polarisation stages of:

(a) subjecting a high $T_1$ agent to a high magnetic field (e.g. 1 T or more) at low temperature (e.g. 100 K or less);

(b) exposing the agent to a $T_1$ shortening effect in order to attain thermodynamic equilibrium at said low temperature.

The $T_1$ shortening effect may be provided by exposure to a variable magnetic field gradient but it may also be achieved by adding magnetic material (e.g. paramagnetic, superparamagnetic or ferromagnetic materials) to the agent during the period when the agent is exposed to low temperature, field cycling to a field allowing cross polarisation, gradually increasing the magnetic field at such a rate that the increase in polarisation of the high $T_1$ agent is maximised, gradually decreasing the temperature at such a rate that the increase in polarisation of the high $T_1$ agent is maximised, or adding a material with unpaired electrons during the period when the high $T_1$ agent is exposed to said low temperature. Possible T1 shortening agents include Gd and NO but preferred $T_1$ shortening agents are $O_2$ and NO which may be conveniently separated from the high $T_1$ agent before transportation and subsequent use.

In the third embodiment of the invention, both the high $T_1$ agent and the aqueous solvent (eg. water) in which it is dissolved may be polarised. This may be carried out at low temperature conveniently in the same magnetic field and after mixing the adminstrable composition should be warmed very rapidly prior to administration.

Thus viewed from a further aspect, the present invention provides an administrable composition comprising a polarised high $T_1$ agent and polarised water.

The high $T_1$ agents used in the method according to the invention may be conveniently formulated with conventional pharmaceutical or veterinary carriers or excipients. Formulations manufactured or used according to this invention may contain, besides the high $T_1$ agent, formulation aids such as are conventional for therapeutic and diagnostic compositions in human or veterinary medicine. Thus the formulation may for example include stabilizers, antioxidants, osmolality adjusting agents, solubilizing agents, emulsifiers, viscosity enhancers, buffers, etc. The formulation may be in forms suitable for parenteral (eg. intravenous or intraarterial) or enteral (eg. oral or rectal) application, for example for application directly into body cavities having external voidance ducts (such as the lungs, the gastrointestinal tract, the bladder and the uterus), or for injection or infusion into the cardiovascular system. However solutions, suspensions and dispersions in physiological tolerable carriers will generally be preferred.

For use in in vivo imaging, the formulation, which preferably will be substantially isotonic, may conveniently be administered at a concentration sufficient to yield a 1 micromolar to 10M concentration of the high $T_1$ agent in the imaging zone; however the precise concentration and dosage will of course depend upon a range of factors such as toxicity, the organ targeting ability of the high $T_1$ agent and the administration route. The optimum concentration for the MR imaging agent represents a balance between various factors. In general, optimum concentrations would in most cases lie in the range 0.1 mM to 10M, preferably more than 10 mM, especially more than 100 mM. Isotonic solution may be especially preferred. In certain circumstances concentrations above 1M are preferred. Formulations for intravenous or intraarterial administration would preferably contain the high $T_1$ agent in concentrations of 10 mM to 10M, especially more than 50 mM. For bolus injection the concentration may conveniently be 0.1 mM to 56M, preferably more than 200 mM, more preferably more than 500 mM. In certain circumstances, the preferred concentration is above 1M, even more preferably above 5M.

Parenterally administrable forms should of course be sterile and free from physiologically unacceptable agents, and should have low osmolality to minimize irritation or other adverse effects upon administration and thus the formulation should preferably be isotonic or slightly hypertonic. Suitable vehicles include aqueous vehicles customarily used for administering parenteral solutions such as Sodium Chloride solution, Ringer's solution, Dextrose solution, Dextrose and Sodium Chloride solution, Lactated Ringer's solution and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The compositions can contain preservatives, antimicrobial agents, buffers and antioxidants conventionally used for parenteral solutions, excipients and other additives which are compatible with the high $T_1$ agents and which will not interfere with the manufacture, storage or use of the products.

Where the high $T_1$ agent is to be injected, it may be convenient to inject simultaneously at a series of administration sites such that a greater proportion of the vascular tree may be visualized before the polarization is lost through relaxation.

The dosages of the high $T_1$ agent used according to the method of the present invention will vary according to the precise nature of the high $T_1$ agents used, of the tissue or organ of interest and of the measuring apparatus. Preferably the dosage should be kept as low as possible while still achieving a detectable contrast effect. In general, the maximum dosage will depend on toxicity constraints.

The invention is illustrated with reference to the following non-limiting Examples and the accompanying drawings in which:

FIG. 5 shows magnetic field versus time.

EXAMPLE 1

Figure 1:
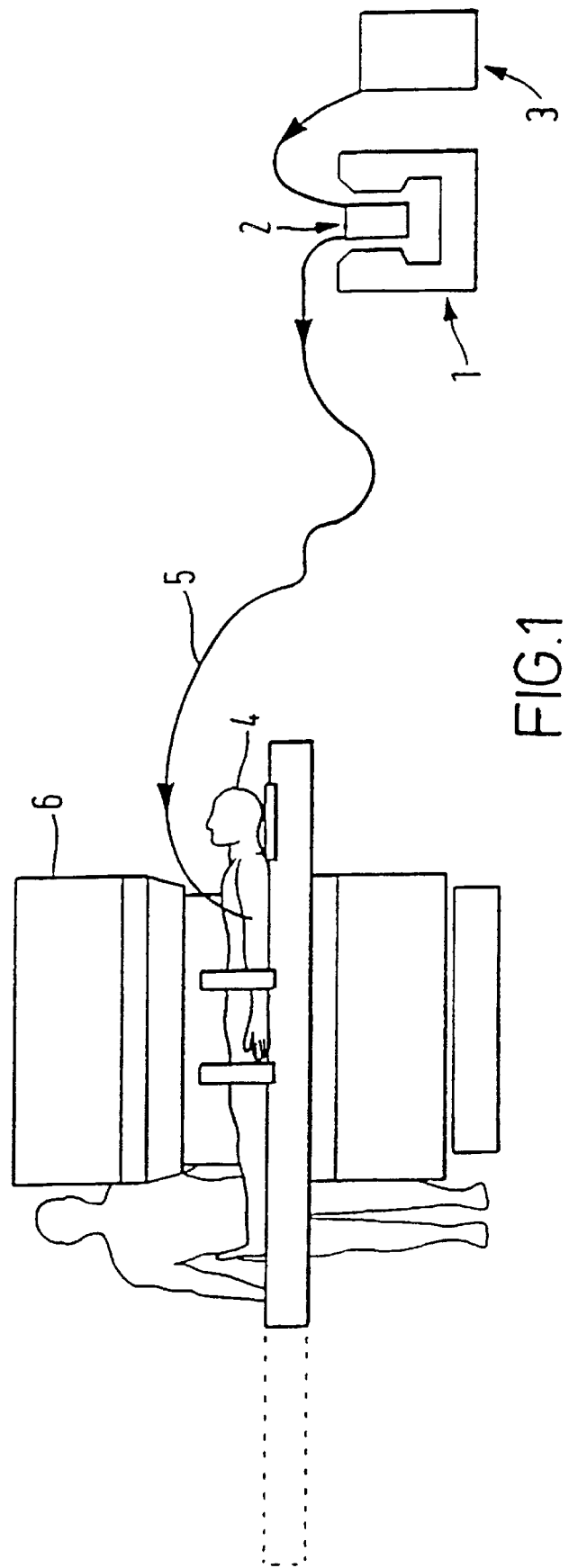
FIG. 1 is a schematic representation of an apparatus suitable for carrying out the first embodiment of the invention.
Figure 2:
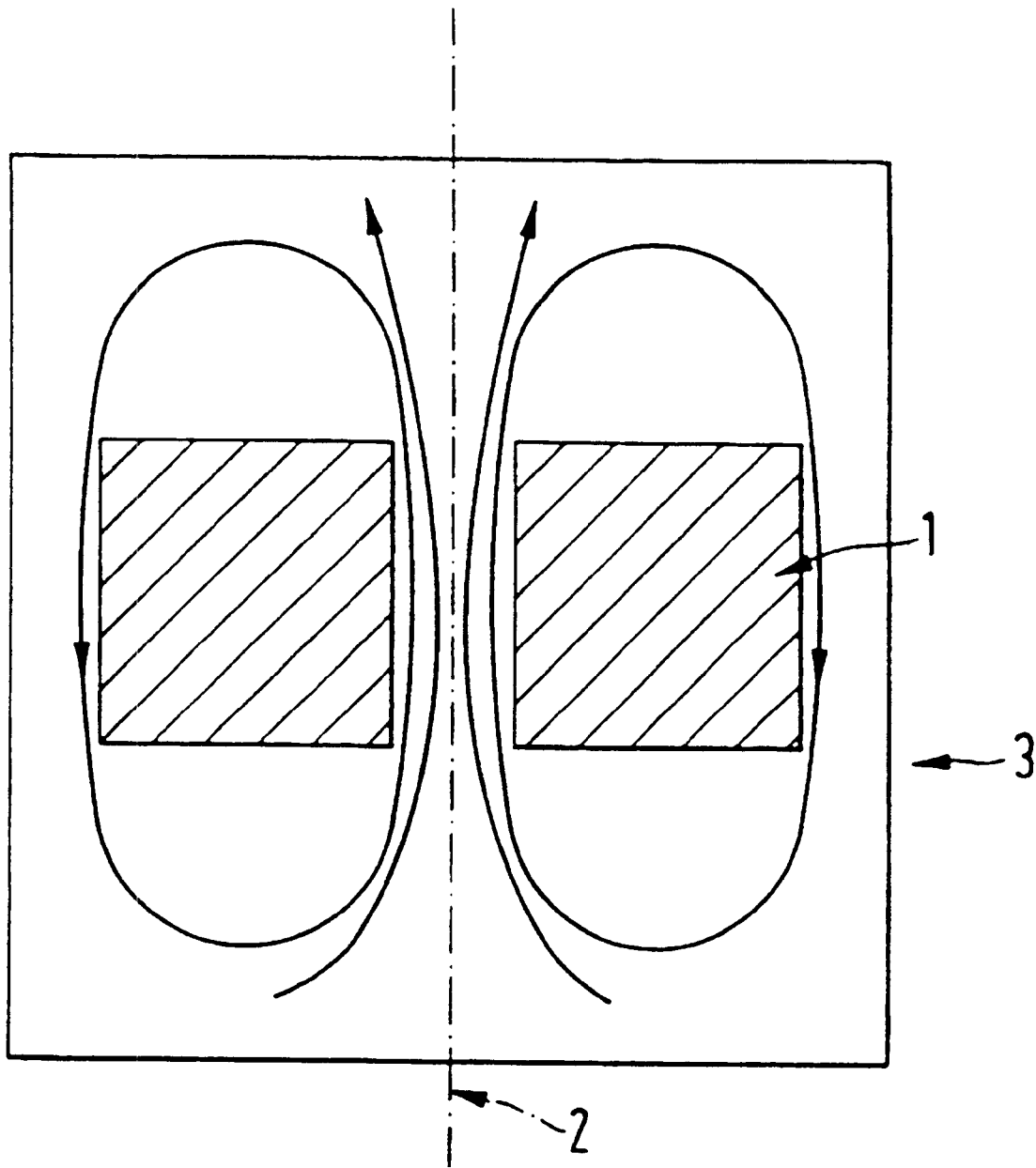
FIG. 2 shows a dielectric resonator (1) (with an axis of rotational symmetry (2)) within a metal box (3)
Figure 3:
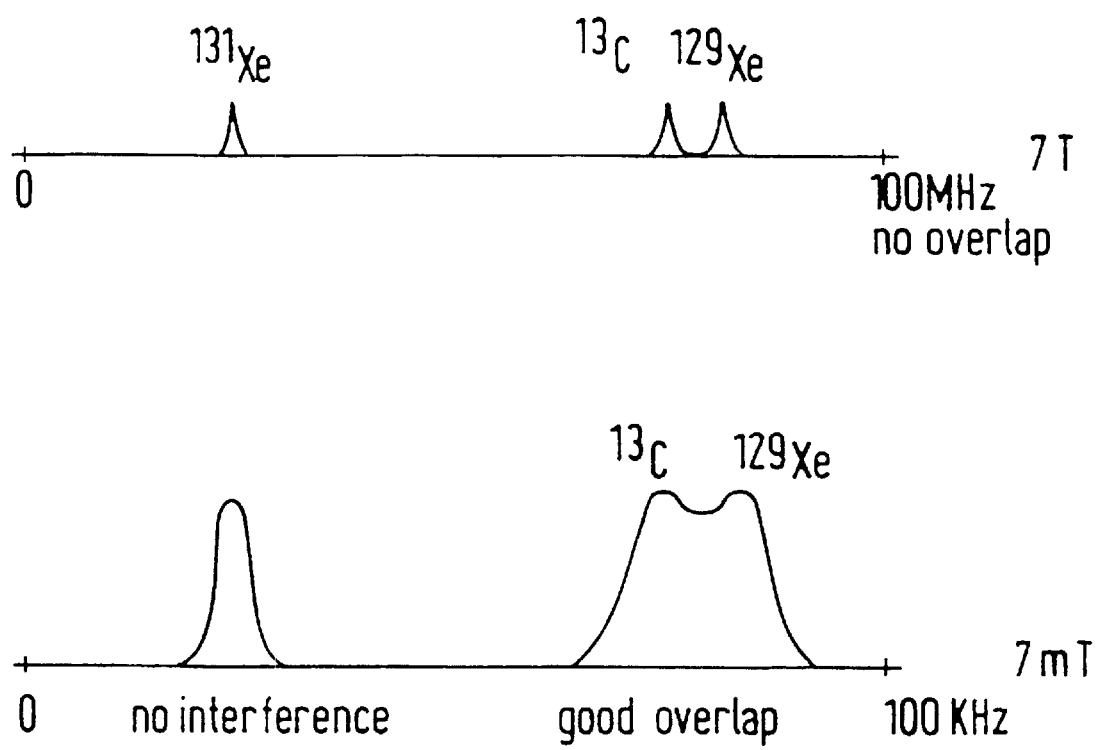
FIG. 3 shows the behaviour of a system at various field strengths.
Figure 4:
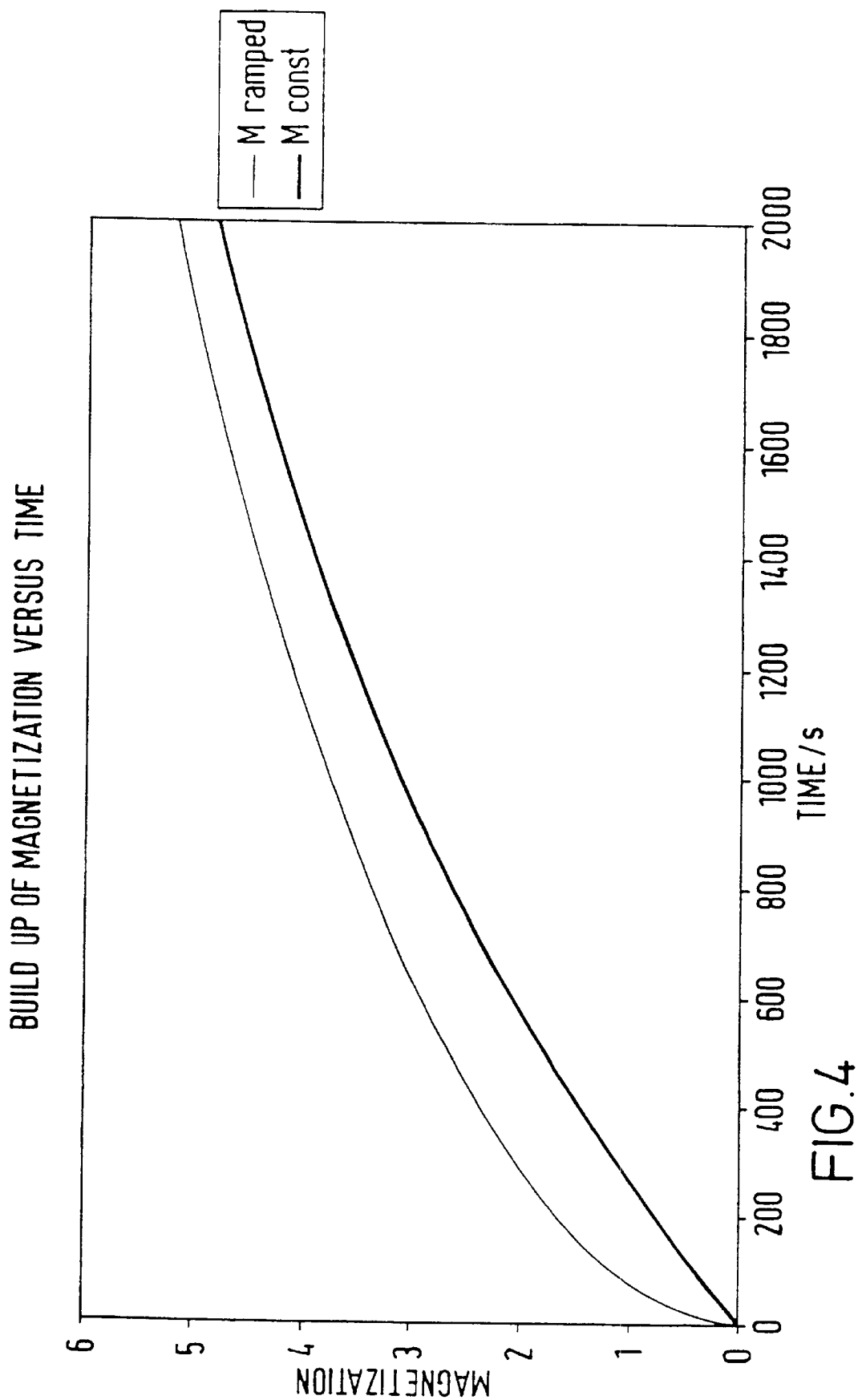
FIG. 4 shows a build-up of magnetisation versus time.

A high $T_1$ agent is placed in a chamber at very low temperature (about 4 K). Fluent $O_2$ is added and crystallised on the surface of the high $T_1$ agent. In a separate chamber, frozen $H_2O$ is subjected to the same treatment as the high $T_1$ agent. Both chambers are placed in a strong magnetic field (about 15 T) and the temperature kept low.

When thermodynamic equilibrium is reached, the temperature is increased to about 200 K. The oxygen disappears as a gas. The high $T_1$ agent and the frozen $H_2O$ are mixed and stored until needed. The temperature is increased and the solution comprising polarised high $T_1$ agent and hyperpolarised water is injected.

EXAMPLE 2

300 mg of sterile $Na_2{}^{13}CO_3$ or $NaH^{13}CO_3$ is placed inside a 10 ml plastic injection syringe. The gas inside the syringe is enriched with >20% oxygen. The syringe is placed inside a magnet (1–20 T) at a temperature of about 4 K (0.001–5 K) until thermodynamic equilibrium is reached.

The syringe is removed and transported to the subject located in the MRI magnet. 10 ml of sterile Ringers Solution (at 37° C., pH 7.4) is aspirated and injected at a rate of 10 ml/sec immediately after the high $T_1$ agent has dissolved. 13C MRI is performed using a fast pulse sequence. $T_1$ in the blood is about 20 s and the distribution of the agent is followed on the MR imager.

EXAMPLE 3

To a sample of sodium acetate (1-$^{13}$C) is added α, γ-bisphenyl-β-phenylallyl benzene complex (5% w/w). The compounds are milled together to give an intimate mixture, which is transferred to a borosilicate glass ampule. This is then repeatedly evacuated and filled with helium. The last time a pressure of a 200 mbar of helium is left in the ampule, which is then flame sealed.

The sample is polarized by microwaves (70 GHz) for at least one hour at a field of 2.5 T at a temperature of 4.2 K. The progress of the polarization process is followed by in situ NMR (fast adiabatic passage). When a suitable level of polarization has been reached, the ampule is rapidly removed from the polarizer and, while handled in a magnetic Field of no less than 50 mT, cracked open and the contents are quickly discharged and dissolved in warm (40° C.) water.

Experiment 1: This solution is quickly transferred to a spectrometer and $^{13}$C spectrum with enhanced intensity is recorded.

Experiment 2: The sample solution is inserted into an MRI machine with $^{13}$C capability and a picture with enhanced intensity and contrast is obtained by a single shot technique.

Experiment 3: The solution is quickly injected into a rat and a $^{13}$C MRI picture with enhanced intensity and contrast is obtained, also in this case, by utilization of a single shot technique.

EXAMPLE 4

To a sample of sodium bicarbonate—$^{13}$C is added $MnCl_2$ (5% w/w). The compounds are milled together to give an intimate mixture, which is transferred to a borosilicate glass ampule. This is then repeatedly evacuated and filled with helium. The last time a pressure of a 200 mbar of helium is left in the ampule, which is then flame sealed.

The sample is polarized by microwaves (70 GHz) for at least 1 hour at a field of 2.5 T at a temperature of 4.2 K. The progress of the polarization process is followed by in situ NMR (fast adiabatic passage). When a suitable level of polarization has been reached, the ampule is rapidly removed from the polarizer and, while handled in a magnetic field of no less than 50 mT, cracked open and the contents are quickly discharged and dissolved in warm (40° C.) water.

Experiment 1: This solution is quickly transferred to a spectrometer and $^{13}$C spectrum with enhanced intensity is recorded.

Experiment 2: The sample solution is inserted into an MRI machine with $^{13}$C capability and a picture with enhanced intensity and contrast is obtained by a single shot technique.

Experiment 3: The solution is quickly injected into a rat and a $^{13}$C MRI picture with enhanced intensity and contrast is obtained, also in this case, by utilization of a single shot technique.

EXAMPLES 5–7
Low-field Pumping of $^{13}$C

EXAMPLE 5

A sample of solid 1-$^{13}$C-2,2,2',2',2",2"-hexadeuterotris(hydroxymethyl)nitromethane was subjected to a magnetic field of 6.56 T at a temperature of 2.5 K for 10 minutes. The sample was then removed from the centre of the magnet to the stray field (7 mT) for a duration 1 s and then returned to the magnet. After another 10 minutes the process was repeated one more. An $^{13}$C-NMR spectrum of the solid sample was recorded and the signal was found to be in accordance with thermal equilibrium at 6.56 T and 2.5 K. $T_1$-values for the $^{13}$C atom in 1-$^{13}$C-2,2,2',2',2",2"-hexadeuterotris(hydroxymethyl)nitromethane

| | |
|---|---|
| $H_2O$, air saturated, 37° C., 7 T | 95 s |
| $H_2O$, degassed, 37° C., 7 T | 102 s |
| Human bloodplasma, 37° C., 7 T | 60 s |
| Solid, 20° C., 7 T | 22 min |
| Solid, −30° C., 7 T | 47 min |
| Solid, 2.5 K, 7 T | 55 hours |

EXAMPLE 6

A sample of solid 1-$^{13}$C-1,1-bis(hydroxydideuteromethyl)-2,2,3,3-tetradeuterocyclopropane was subjected to a magnetic field of 6.56 T at a temperature of 2.5 K for 10 minutes. The sample was then removed from the centre of the magnet to the stray field (7 mT) for a duration of 1 s and then returned to the magnet. After another 10 minutes the process was repeated one more. A $^{13}$C-NMR spectrum of the solid sample was recorded and the signal was found to be in accordance with thermal equilibrium at 6.56 T and 2.5 K.

EXAMPLE 7

A sample of solid 2-$^{13}$C-2,2-bis(trideuteromethyl)-1,1,3,3-tetradeuteropropane-1,3-diol was subjected to a magnetic field of 6.56 T at a temperature of 2.5 K for 10 minutes. The sample was then removed from the centre of the magnet to the stray field (7 mT) for a duration 1 s and then returned to the magnet. After another 10 minutes the process was repeated once more. An 13C-NMR spectrum of the solid sample was recorded and the signal was found to be in accordance with thermal equilibrium at 6.56 T and 2.5 K. T1-values for the $^{13}$C atom in 2-$^{13}$C-2,2-bis(trideuteromethyl)-1,1,3,3-tetradeuteropropane-1,3-diol

| | |
|---|---|
| $H_2O$, air saturated, 37° C., 7 T | 133 s |
| $H_2O$, degassed, 37° C., 7 T | 157 s |
| Human bloodplasma, 37° C., 7 T | 96 s |
| Solid, 20° C., 7 T | 237 s |
| Solid, 2.5 K, 7 T | 45 hours |

EXAMPLES 8–9
Solution Experiments

EXAMPLE 8

A sample of solid 1-$^{13}$C-2,2,2',2',2",2"-hexadeuterotris(hydroxymethyl)nitromethane (20 mg) was subjected to the above-mentioned pumping procedure (see Examples 5–7) and then in less than 1 second moved to a holding field of 0.4 T where also a sample of deuterium oxide (3 ml) at a temperature of 40° C., stirred by nitrogen bubbling, was kept. The solid was added to the liquid and a clear solution was obtained in less than 1 S. This solution was pipetted over to a 5 mm standard NMR-sample tube and moved to a nearby NMR-spectrometer while kept in a holding field of 10 mT. The sample was inserted into the spectrometer and a $^{13}$C-spectrum was recorded. The whole process of moving the sample out of the cryomagnet, dissolution, sample preparation, transport and spectroscopy took 35 s. The intensity of the $^{13}$C-signal was compared to the intensity after the sample had reached thermal equilibrium at 40° C. and 7 T. An enhancement factor of 12 was found.

EXAMPLE 9

A sample of solid 2-$^{13}$C-2,2-bis(trideuteromethyl)-1,1,3,3-tetradeuteropropane-1,3-diol (20 mg) was subjected to the above-mentioned pumping procedure (see Examples 5–7) and then in less than 1 second moved to a holding field of 0.4 T where also a sample of deuterium oxide (3 ml) at a temperature of 40° C., stirred by nitrogen bubbling, was kept. The solid was added to the liquid and a clear solution was obtained in less than 1 S. This solution was pipetted over to a 5 mm standard NMR-sample tube and moved to a nearby NMR-spectrometer while kept in a holding field of 10 mT. The sample was inserted into the spectrometer and a $^{13}$C-spectrum was recorded. The whole process of moving the sample out of the cryomagnet, dissolution, sample preparation, transport and spectroscopy took 35 s. The intensity of the $^{13}$C-signal was compared to the intensity after the sample had reached thermal equilibrium at 40° C. and 7 T. An enhancement factor of 21 was found.

What is claimed is:
1. A method of magnetic resonance (MR) investigation of a sample, said method comprising:
(i) producing a hyperpolarised solution of a high $T_1$ agent by dissolving in a physiologically tolerable solvent a hyperpolarised solid sample of said high $T_1$ agent;

(ii) where the hyperpolarisation of the solid sample of said high $T_1$ agent in step (i) is effected by means of a polarising agent, optionally separating the whole, substantially the whole, or a portion of said polarising agent from said high $T_1$ agent;

(iii) administering said hyperpolarised solution to said sample;

(iv) exposing said sample to radiation of a frequency selected to excite nuclear spin transitions in an MR imaging nuclei of the high $T_1$ agent;

(v) detecting magnetic resonance signals from said sample; and (vi) optionally, generating an image, dynamic flow data, diffusion data, perfusion data, physiological data or metabolic data from said detected signals, wherein said high $T_1$ agent in said hyperpolarised solution has a $T_1$ value (at a field strength in the range 0.01–5 T and a temperature in the range 20–40° C.) of at least 5 seconds and wherein said high $T_1$ agent is $^{13}C$ enriched at one or more carbonyl or quaternary carbon positions.

2. A method as claimed in claim 1 wherein said high $T_1$ agent or the hyperpolarised solution thus formed is transported in a magnetic field and at low temperature between steps (i) and (ii) and such that said agent or said solution retains its polarisation during said transportation.

3. A method as claimed in claim 2 wherein the magnetic field during said transportation is greater than 10 mT.

4. A method as claimed in claim 2 wherein the magnetic field during said transportation is greater than 1 T.

5. A method as claimed in claim 2 wherein the temperature during said transportation is lower than 80 K.

6. A method as claimed in claim 1 wherein during said dissolution step (i), the high $T_1$ agent is soluble in said physiologically tolerable solvent to a concentration of at least 1 mM at a rate of 1 mM/3 $T_1$.

7. A method as claimed in claim 6 wherein said high $T_1$ agent is soluble in said physiologically tolerable solvent to a concentration of at least 1 mM at a rate of 1 mM/$T_1$.

8. A method as claimed in claim 1 wherein a magnetic field is present during the dissolution stage and wherein said magnetic field is greater than 10 mT.

9. A method as claimed in claim 1 wherein step (i) comprises polarising a solid high $T_1$ agent by irradiating a polarising agent whereby to cause dynamic nuclear polarisation.

10. A method as claimed in claim 1 wherein said high $T_1$ agent has a $T_1$ value (at a field strength of 0.01–5 T and a temperature in the range 20–40° C.) of at least 10 secs.

11. A method as claimed in claim 1 wherein said high $T_1$ agent exhibits a chemical shift of more than 2 ppm per 2 pH units.

12. A method as claimed in claim 11 wherein said chemical shift is per Kelvin.

13. A method as claimed in claim 11 wherein said chemical shift is upon being metabolised.

14. A method of magnetic resonance (MR) investigation of a sample, said method comprising:

(i) producing a hyperpolarised solution of a high $T_1$ agent by dissolving in a physiologically tolerable solvent a hyperpolarised solid sample of said high $T_1$ agent;

(ii) where the hyperpolarisation of the solid sample of said high $T_1$ agent in step (i) is effected by means of a polarising agent, separating the whole, substantially the whole, or a portion of said polarising agent from said high $T_1$ agent;

(iii) administering said hyperpolarised solution to said sample;

(iv) exposing said sample to radiation of a frequency selected to excite nuclear spin transitions in an MR imaging nuclei of the high $T_1$ agent;

(v) detecting magnetic resonance signals from said sample; and (vi) optionally, generating an image, dynamic flow data, diffusion data, perfusion data, physiological data or metabolic data from said detected signals, wherein said high $T_1$ agent in said hyperpolarised solution has a $T_1$ value (at a field strength in the range 0.01–5 T and a temperature in the range 20–40° C.) of at least 5 seconds, and wherein step i) comprises polarising a hyperpolarisable gas before, during or after introducing said high $T_1$ agent thereto whereby to cause nuclear polarisation of said high $T_1$ agent.

15. A method as claimed in claim 14 wherein said high $T_1$ agent has a $T_1$ value (at a field strength of 0.01–5T and a temperature in the range 20–40° C.) of at least 10 secs.

16. A method as claimed in claim 14 wherein said high $T_1$ agent contains $^{13}C$, $^{15}N$, $^{29}Si$, $^{31}P$, $^{1}H$ or $^{19}F$ nuclei.

17. A method as claimed in claim 16 wherein said high $T_1$ agent is $^{13}C$ enriched at one or more carbonyl or quaternary carbon positions.

18. A method as claimed in claim 14 wherein said high $T_1$ agent exhibits a chemical shift of more than 2 ppm per 2 pH units.

19. A method as claimed in claim 18 wherein said chemical shift is per Kelvin.

20. A method as claimed in claim 18 wherein said chemical shift is upon being metabolised.

21. A method as claimed in claim 14 wherein said high $T_1$ agent has $^{13}C$ or $^{15}N$ or $^{29}Si$ at one particular position in its molecular structure in an amount above 5%.

22. A method as claimed in claim 14 wherein said high $T_1$ agent has $^{13}C$ or $^{15}N$ or $^{29}Si$ at one particular position in its molecular structure in an amount above 99%.

23. A method as claimed in claim 14 wherein said hyperpolarisable gas is a noble gas.

24. A method as claimed in claim 14 wherein said hyperpolarisable gas is a mixture of two or more gases.

25. A method of magnetic resonance (MR) investigation of a sample, said method comprising:

(i) producing a hyperpolarised solution of a high $T_1$ agent by dissolving in a physiologically tolerable solvent a hyperpolarised solid sample of said high $T_1$ agent;

(ii) where the hyperpolarisation of the solid sample of said high $T_1$ agent in step (i) is effected by means of a polarising agent, optionally separating the whole, substantially the whole, or a portion of said polarising agent from said high $T_1$ agent;

(iii) administering said hyperpolarised solution to said sample;

(iv) exposing said sample to radiation of a frequency selected to excite nuclear spin transitions in an MR imaging nuclei of the high $T_1$ agent;

(v) detecting magnetic resonance signals from said sample; and (vi) optionally, generating an image, dynamic flow data, diffusion data, perfusion data, physiological data or metabolic data from said detected signals, wherein said high $T_1$ agent in said hyperpolarised solution has a $T_1$ value (at a field strength in the range 0.01–5 T and a temperature in the range 20–40° C.) of at least 5 seconds, and wherein step i) comprises the polarisation stages of:
a) subjecting said high $T_1$ agent to a high magnetic field at low temperature;
b) exposing the agent to a $T_1$ shortening effect in order to attain thermodynamic equilibrium at said low temperature.

26. A method as claimed in claim 25 wherein said magnetic field of stage (a) of step (i) is greater than 1 T.

27. A method as claimed in claim 25 wherein said low temperature of stage (a) of step (i) is 100 K or less.

28. A method as claimed in claim 25 wherein said $T_1$ shortening effect is provided by exposure to a variable magnetic field gradient.

29. A method as claimed in claim 25 wherein said $T_1$ shortening effect is provided by field cycling to a field allowing cross polarisation.

30. A method as claimed in claim 25 wherein said $T_1$ shortening effect is provided by gradually increasing the magnetic field at such a rate that the increase in polarisation of the high $T_1$ agent is maximised.

31. A method as claimed in claim 25 wherein said $T_1$ shortening effect is provided by gradually decreasing the temperature at such a rate that the increase in polarisation of the high $T_1$ agent is maximised.

32. A method as claimed in claim 25 wherein said $T_1$ shortening effect is provided by adding a material with unpaired electrons during stage (a) of step (i) when the agent is exposed to low temperature.

33. A method of magnetic resonance MR investigation of a sample, said method comprising:
i) producing solid hyperpolarised $^{129}Xe$ by irradiating a polarising agent whereby to cause dynamic nuclear polarisation;
ii) dissolving said solid hyperpolarised $^{129}Xe$ in a physiologically tolerable solvent to form a solution;
iii) administering said solution of said hyperpolarised $^{129}Xe$ in a physiologically tolerable solvent to said sample; and
iv) detecting magnetic resonance signals from said sample.

34. A method as claimed in claim 25 wherein said high $T_1$ agent contains $^{13}C$, $^{15}N$, $^{29}Si$, $^{31}P$, $^{1}H$ or $^{19}F$ nuclei.

* * * * *